United States Patent
Drevets et al.

(10) Patent No.: US 10,098,854 B2
(45) Date of Patent: Oct. 16, 2018

(54) METHOD FOR THE TREATMENT OF DEPRESSION

(71) Applicant: Janssen Pharmaceutica NV, Beerse (BE)

(72) Inventors: Wayne C. Drevets, Newton, PA (US); Qingqin S. Li, Flemington, NJ (US)

(73) Assignee: Janssen Pharmaceutica NV (BE)

( * ) Notice: Subject to any disclaimer, the term of this patent is extended or adjusted under 35 U.S.C. 154(b) by 29 days.

(21) Appl. No.: 14/824,513

(22) Filed: Aug. 12, 2015

(65) Prior Publication Data

US 2016/0045455 A1 Feb. 18, 2016

Related U.S. Application Data

(60) Provisional application No. 62/036,896, filed on Aug. 13, 2014.

(51) Int. Cl.
*C12Q 1/68* (2018.01)
*A61K 31/135* (2006.01)
*C12Q 1/6883* (2018.01)

(52) U.S. Cl.
CPC .......... *A61K 31/135* (2013.01); *C12Q 1/6883* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,543,434 A | 8/1996 | Weg |
| 6,040,479 A | 3/2000 | Steiner et al. |
| 6,176,242 B1 | 1/2001 | Rise |
| 7,273,889 B2 | 9/2007 | Mermelstein |
| 7,687,080 B2 | 3/2010 | Wolicki |
| 7,973,043 B2 | 7/2011 | Migaly |
| 2004/0214215 A1 | 10/2004 | Yu et al. |
| 2006/0276550 A1 | 12/2006 | Bhagwat |
| 2007/0287753 A1 | 12/2007 | Charney et al. |
| 2009/0306137 A1 | 12/2009 | Wolfgang et al. |
| 2011/0112131 A1 | 5/2011 | Holtman et al. |
| 2011/0306674 A1 | 12/2011 | Schiene et al. |
| 2012/0225949 A1 | 9/2012 | Papalos |
| 2013/0172361 A1 | 7/2013 | Fava et al. |
| 2013/0236573 A1 | 9/2013 | Singh et al. |
| 2014/0093592 A1 | 4/2014 | Jaskaran et al. |
| 2014/0256821 A1 | 9/2014 | Charney et al. |
| 2016/0332962 A1 | 11/2016 | Chen et al. |
| 2016/0338977 A1 | 11/2016 | Singh et al. |

FOREIGN PATENT DOCUMENTS

| | | |
|---|---|---|
| DE | 2062620 | 7/1971 |
| DE | 4312016 A1 | 10/1994 |
| DE | 19619665 | 11/1997 |
| DE | 102007009888 A1 | 9/2008 |
| EP | 1103256 A1 | 5/2001 |
| JP | 63002932 A | 1/1988 |
| WO | 199423711 A1 | 10/1994 |
| WO | 200004875 A2 | 2/2000 |
| WO | 2007111880 A2 | 10/2007 |
| WO | 2011020061 A2 | 2/2011 |
| WO | 2014031975 | 2/2014 |
| WO | 2014169272 | 10/2014 |

OTHER PUBLICATIONS

Tansey et al; Biol Psychiatry, vol. 73, 2013, pp. 679-682.*
Diazgranados_et_al, Rapid Resolution of Suicidal ideation After a Single Infusion of an N-Methyl-D Aspartate Antagonist in Pateient With Treatment-Resistant Majar Depressive Disorder, J Clin Psychiatry, 2010, pp. 1605-1611, vol. 71 Issue 12, Physicians Postgraduate Press.
Gomes,et al., Neurotoxicity of Subarachnoid Preservative—Frees (+)-Ketamine in Dogs, Pain Physician, 2011, pp. 83-90, vol. 14.
Hijazi,et al., Stability of Ketamine and Its metabolites Norketamine and Dehydronorketamine in Human Biological Samples, Clinical Chemistry, 2001, pp. 1713-1715, vol. 47 Issue 9.
Ho,et al., In vitro effects of preservatives in nasal sprays on human nasal epithelial cells, American Journal of Rhinology, 2008, pp. 125-129, vol. 22.
Hong,et al., Allergy to ophthalmic preservatives, Current Opinion in Allergy and Clinical Immunology, 2009, pp. 447-453, vol. 9.
Huang,et al., Mechanism of nasal Absorption of Drugs I: Physicochemical Parameters Influencing the rate of In Situ Nasal Absorption of Drugs in Rats, Journal of Pharmaceutical Science, Feb. 27, 1985, pp. 608-611, vol. 74 Issue 6.
Huge,et al., Effects of low—dose intranasal (S)- ketamine in patients with neuropathic pai, European Journal of Pain, Sep. 3, 2009, pp. 387-394, vol. 14, Elsevier Ltd.
Johansson,et al., Prehospital analgesia using nasal administration of S-ketamine-a case series, Scandinavian Journal of Trauma, 2013, pp. 1-5, vol. 21 Issue 38, BioMed Central Ltd.
Logan,et al., Immobilizing Wild Mountain Lions ( Fells Concolor) with Ketamine hydrochloride and Xylazine Hydrochloride, Journal of Wildlife Diseases, 1986, pp. 97-103, vol. 22 Issue 1.
Marhofer, et al, S( +)-Ketamine for caudal block in paediatric anaesthesia, British Journal of Anaesthesia, 2000, pp. 341-345, vol. 84 Issue 3.
Mathew_et_al, Ketamine for Treatment-Resistant Unipolar Depression, CNS Drugs, 2012, pp. 189-204, vol. 26 Issue 3, Adis Data Information BV.
Noppers_et_al, Absence of long-term analgesic effect from a short-term S-ketamine infusion on fibromyalgia pain: A randomized, prospective, double blind, active placebo-controlled trial, European Journal of Pain, Apr. 11, 2011, pp. 942-949, vol. 15, Elsevier Ltd.
Oishi,et al., Effects of propyl paraben on the male reproductive system, Food and Chemical Toxicology, Jul. 7, 2002, pp. 1807-1813, vol. 40, Elsevier Science Ltd.

(Continued)

*Primary Examiner* — Jehanne S Sitton

(57) ABSTRACT

The present invention is directed to method for the treatment of depression, for example, treatment resistant depression; wherein the treatment regimen is adjusted depending on the patient's genotype at SNP rs4306882.

6 Claims, No Drawings

Specification includes a Sequence Listing.

(56) References Cited

OTHER PUBLICATIONS

Okamoto_et_al, Rapid Antidepressant Effect of Ketamine Anesthesia During Electroconvulsive Therapy of Treatment-Resistant Depression, Journal of ECT, 2010, pp. 223-227, vol. 26 Issue 3, Lippincott Williams & Wilkins.
Paslakis_et_al, Oral Administration of the NMDA Receptor Antagonist S-Ketamine as Add-On Therapy of Depression: A Case Series, Pharmacopsychiatry, 2010, pp. 33-35, vol. 43.
Paul_et_al, Comparison of racemic ketamine and S-ketamine in treatment-resistant major depression: Report of two cases, The World Journal of Biological Psychiatry Sep. 28, 2007, pp. 241-244, vol. 10 Issue 3, Informa UK Ltd.
Pfizer, (S)-(+)-Ketamine Hydrochloride Solution, Material Safety Data Sheet, Nov. 5, 2008, pp. 1-8, Version 1.0.
PRD3253CLPCT_Opposition Brief Translation, 2014.
Price_et_al, Effects of Intravenous Ketamine on Explicit and Implicit Measures of Suicidality in Treatment-Resistant Depression, BIOL PSYCHIATRY, 2009, pp. 522-526, vol. 66, Society of Biological Psychiatry.
Sarchiapone, et al., Association of Polymorphism (Val66met) of Brain-Derived Neurotrophic Factor with Sucide Attempts in Depressed Patients, Neuropsychobiology, Jul. 7, 2008, pp. 139-145, vol. 57.
Skolnick_et_al, Glutamate-based antidepressants: 20 years on, Trends in Pharmacological Sciences, 2006, pp. 563-569, vol. 30 Issue 11.
Soni,et al., Safety assessment of esters of p-hydroxybenzoic acid (parabens, Food and Chemical Toxicology, Jan. 31, 2005, pp. 985-1015, vol. 43, Elsevier Ltd.
Soni,et al., Safety assessment of propyl paraben: a review of the published literature, Food and Chemical Toxicology, Sep. 25, 2000, pp. 513-532, vol. 39, Elsevier Science LTD.
Stevenson, Ketamine:A Review, Update in Anaesthesia, 2005, pp. 25-29, vol. 20.
Tansey et al., Contribution of Common Genetic Variants to Antidepressant Response, BIOL PSYCHIATRY, 2013, 679-682, 73.
Vranken_et_al, Iontophoretic administration of S(C)-ketamine in patients with intractable central pain: A placebo-controlled trial, Pain, Aug. 15, 2005, pp. 224-231, vol. 118, Elsevier B.V.
Washington,et al., Determination of baseline human nasal pH and the effect of intranasally administered buffers, International Journal of Pharmaceutics, Nov. 24, 1999, pp. 139-146, vol. 198, Elsevier Science B.V.
White _et_al, Pharmacology of Ketamine Isomers in surgical Patients, Anesthesiology, 1980, pp. 231-239, vol. 52, The American Society of Anesthesiologists.
White,et al., Comparative Pharmacology of ketamine Isomers, British Journal of Anaesthesia, 1985, pp. 197-203, vol. 57 Issue 2.
WIKIPEDIA, Esketamine, Wikipedia, Sep. 1, 2015, pp. 1-4, Wikipedia.
Clinical Trials.Gov _NCT01998958, A Study to Evaluate the Safety and Efficacy of Intranasal Esketamine in Treatment-resistant Depression. ClinicaiTrials.gov Identifier: NCT01998958. Jul. 14, 2014 [online]. [Retrieved on Sep. 23, 2015]. Retrieved from the Internet: <URL: https://clinicaltrials.gov/archive/NCT01998958/2014_07 14> PDF FILE: p. 1-40. p. 1, Brief Summary, Phase, and the last para; and p. 2, para 1 and 3.
GENBANK_AC099753, *Homo sapiens* chromosome 3 clone RP11-466A13, complete sequence. Mar. 20, 2002, [online]. [Retrieved on Oct. 1, 2015]. Retrieved from the Internet: <URL: http://www.ncbi.nlm.nih.gov/nuccore/19551144/> Pdf file: p. 1-40. p. 1, Definition; p. 3, Origin, p. 27, the nucleotide sequence between 113924-112924, especially the nucleotides between 113.444-113405; and the nucleotide at the position of 113424.
Gonzalo Laje et al: "Correspondence Brain-Derived Neurotrophic Factor Val66Met Polymorphism and Antidepressant Efficacy of Ketamine in Depressed Patients", BIOL PSYCHIATRY, vol. 72, No. 11, Dec. 1, 2012 (Dec. 1, 2012), pp. e27-e28.
Anonymous: "NCT02133001 on Jun. 23, 2014: ClinicalTrials.gov Archive", Jun. 23, 2014 (Jun. 23, 2014), pp. 1-6, XP055230128, Retrieved from the Internet: URL:https://clinicaltrials.gov/archive/NCT 02133001/2014_06_23.
Salvadore G ED-Sanacora Gerard et al: "Impact of the Val66Met Polymorphism of Brain-Derived Neurotrophic Factor on Esketamine and Ketamine Antidepressant Effects in Patients with Treatment-Resistant Depression", Biological Psychiatry, Elsevier Science, Newyork, NY; US, vol. 77, No. 9 supplement, May 1, 2015 (May 1, 2015), p. 360S.
International Search Report re: PCT/US2013/030476 dated Apr. 24, 2013.
International Search Report re: PCT/US2014/027059 dated Jul. 16, 2014.
International Search Report re: PCT/US2014/027074 dated May 27, 2014.
International Search Report re: PCT/US2015/44830 dated Nov. 23, 2015.
International Search Report re: PCT/US2015/049961 dated Jan. 12, 2016.
International Search Report re: PCT/EP2016/060922 dated Jul. 28, 2016.
International Search Report re: PCT/US2016/33404 dated Aug. 16, 2016.

\* cited by examiner

METHOD FOR THE TREATMENT OF DEPRESSION

CROSS REFERENCE TO RELATED APPLICATIONS

This application claims the benefit of priority under 35 U.S.C. § 119(e) to U.S. Provisional Application 62/036,896, filed Aug. 13, 2014, the disclosure of which is herein incorporated by reference in its entirety.

SEQUENCE LISTING

The instant application contains a Sequence Listing which has been submitted electronically in ASCII format and is hereby incorporated by reference in its entirety. Said ASCII copy, created on Aug. 11, 2015, is named "PRD3345USNP_SeqListing.txt" and is 56 kilobytes in size.

FIELD OF THE INVENTION

The present invention is directed to method for the treatment of depression, for example, treatment resistant depression; wherein the treatment regimen is adjusted depending on the patient's genotype at SNP rs4306882.

BACKGROUND OF THE INVENTION

Major Depressive Disorder is defined as the presence of one of more major depressive episodes that are not better accounted for psychotic disorder or bipolar disorder. A major depressive episode is characterized by meeting five or more of the following criteria during the same 2 week period which represent a change in functioning and include at least depressed/sad mood or loss of interest and pleasure, indifference or apathy, or irritability and is usually associated with a change in a number of neurovegetative functions, including sleep patterns, appetite and body weight, motor agitation or retardation, fatigue, impairment in concentration and decision making, feelings of shame or guilt, and thoughts of death or dying (Harrison's Principles of Internal Medicine, 2000). Symptoms of a depressive episode include depressed mood; markedly diminished interest or pleasure in all, or almost all, activities most of the day; weight loss when not dieting or weight gain, or decrease or increase in appetite nearly every day; insomnia or hypersomnia nearly every day; psychomotor agitation or retardation nearly every day; fatigue or loss of energy nearly every day; feelings of worthlessness or excessive or inappropriate guilt nearly every day; diminished ability to think or concentrate, or indecisiveness, nearly every day; recurrent thoughts of death, recurrent suicidal ideation without a specific plan, or a suicide attempt or a specific plan for committing suicide. Further, the symptoms cause clinically significant distress or impairment in social, occupational, or other important areas of functioning. (*Diagnostic and Statistical Manual of Mental Disorders*, 4$^{th}$ Edition, American Psychiatric Association, 1994)

Current treatment options for unipolar depression include monotherapy or combination therapy with various classes of drugs including mono-amine oxidase inhibitors (MAOI), tricyclic antidepressants (TCA), serotonin specific reuptake inhibitors (SSRI), serotonin noradrenergic reuptake inhibitors (SNRI), noradrenaline reuptake inhibitor (NRI), "natural products" (such as Kava-Kava, St. John's Wort), dietary supplement (such as s-adenosylmethionine) and others. More specifically, drugs used in the treatment of depression include, but are not limited to imipramine, amitriptyline, desipramine, nortriptyline, doxepin, protriptyline, trimipramine, maprotiline, amoxapine, trazodone, bupropion, chlomipramine, fluoxetine, citalopram, sertraline, paroxetine, tianeptine, nefazadone, venlafaxine, desvenlafaxine, duloxetine, reboxetine, mirtazapine, phenelzine, tranylcypromine, and/or moclobemide. Several of these agents including, but not limited to, serotonin reuptake inhibitors are also used when depression and anxiety co-exist, such as in anxious depression.

In the clinic, 40-50% of depressed patients who are initially prescribed antidepressant therapy do not experience a timely remission of depression symptoms. This group typifies level 1 treatment-resistant depression, that is, a failure to demonstrate an "adequate" response to an "adequate" treatment trial (that is, sufficient intensity of treatment for sufficient duration). Moreover, about approximately 30% of depressed patients remain partially or totally treatment-resistant to at least two antidepressant treatments including combination treatments. Increasingly, treatment of treatment-resistant depression includes augmentation strategies including treatment with pharmacological agents such as, antipsychotics (such as quetiapine, aripiprazole, olanzapine, risperidone, and the like), lithium, carbamazepine, and triiodothyronine, and the like; adjunctive electroconvulsive therapy; adjunctive transcranial magnetic stimulation; etc.

Suicide, also known as completed suicide, is the "act of taking one's own life". Attempted suicide or non-fatal suicidal behavior is self-injury with the desire to end one's life that does not result in death. Suicidal ideations are thoughts of ending one's life but not taking any active efforts to do so.

Suicidal ideation is the medical term for thoughts about or an unusual preoccupation with suicide. The range of suicidal ideation varies greatly from fleeting to detailed planning, role playing, and unsuccessful attempts, which may be deliberately constructed to fail or be discovered, or may be fully intended to result in death. Although most people who undergo suicidal ideation do not go on to make suicide attempts, a significant proportion do. Suicidal ideation is generally associated with depression; however, it seems to have associations with many other psychiatric disorders, life events, and family events, all of which may increase the risk of suicidal ideation.

Suicidal ideation—may include, for example, suicidal thoughts—but may also include other related signs and symptoms. Some symptoms or co-morbid conditions may include unintentional weight loss, feeling helpless, feeling alone, excessive fatigue, low self-esteem, presence of consistent mania, excessively talkative, intent on previously dormant goals, feel like one's mind is racing. The onset of symptoms like these with an inability to get rid of or cope with their effects, a possible form of psychological inflexibility, is one possible trait associated with suicidal ideation. They may also cause psychological distress, which is another symptom associated with suicidal ideation. Symptoms like these related with psychological inflexibility, recurring patterns, or psychological distress may in some cases lead to the onset of suicidal ideation. Other possible symptoms and warning signs include: hopelessness, anhedonia, insomnia, depression, severe anxiety, angst, impaired concentration, psychomotor agitation, panic attack and severe remorse.

Scales used in the evaluation of suicidal ideation include Beck Scale for Suicide Ideation (BSS), Columbia Suicide Severity Rating Scale and The Kessler Psychological Distress Scale (K10, which test does not measure suicidal ideation directly, but there may be value in its administration as an early identifier of suicidal ideation. High scores of psychological distress are also, in some cases associated with suicidal ideation.

There are also several psychiatric disorders that appear to be comorbid with suicidal ideation or considerably increase the risk of suicidal ideation. The following disorders have been shown to be the strongest predictors of suicidal ideation/disorders in which risk is increased to the greatest extent: major depressive disorder (MDD), dysthymia, bipolar disorder, post traumatic stress disorder (PTSD), personality disorders, psychosis (anxiety or detachment from reality), paranoia, schizophrenia and drug abuse.

The main treatments for suicidality and/or suicidal ideation include: hospitalization, outpatient treatment, and medication. Hospitalization allows the patient to be in a secure, supervised environment to prevent their suicidal ideation from turning into suicide attempts. In most cases, individuals have the freedom to choose which treatment they see fit for themselves. However, there are several circumstances in which individuals can be hospitalized involuntarily, including circumstances where an individual poses danger to self or others and where an individual is unable to care for one's self.

Outpatient treatment allows individuals to remain at their place of residence and receive treatment when needed or on a scheduled basis. Before allowing patients the freedom that comes with outpatient treatment, physicians evaluate several factors of the patient. These factors include the patient's level of social support, impulse control and quality of judgment. After the patient passes the evaluation, they are often asked to consent to a "no-harm contract". This is a contract formulated by the physician and the family of the patient. Within the contract, the patient agrees not to harm themselves, to continue their visits with the physician, and to contact the physician in times of need. These patients are then checked on routinely to assure they are maintaining their contract and staying out of troublesome activities.

There are also a number of different pharmacological treatment options for those experiencing suicidal ideation. However, prescribing medication to treat suicidal ideation can be difficult. One reason for this is because many medications lift patients' energy levels before lifting their mood. This puts them at greater risk of following through with attempting suicide. Additionally, if a patient has a co-morbid psychiatric disorder, it may be difficult to find a medication that addresses both the psychiatric disorder and suicidal ideation. Therefore, the medication prescribed to one suicidal ideation patient may be completely different than the medication prescribed to another patient. However, there are several medications that seem to work fairly well for treating suicidal ideation, more particularly antidepressants, including fluoxetine (PROZAC), sertraline (ZOLOFT), paroxetine (PAXIL), fluvoxamine (LUVOX), venlafaxine (EFFEXOR) and nefazodone (SERZONE).

Although research is largely in favor of the use of antidepressants for the treatment of suicidal ideation, in some cases antidepressants are claimed to be associated with increased suicidal ideation. Upon the start of using antidepressants, many clinicians will note that sometimes the sudden onset of suicidal ideation may accompany treatment. This has caused the Food and Drug Administration (FDA) to issue a warning stating that sometimes the use of antidepressants may actually increase the thoughts of suicidal ideation.

Ketamine (a racemic mixture of the corresponding S- and R-enantiomers) is an NMDA receptor antagonist, with a wide range of effects in humans, including analgesia, anesthesia, hallucinations, dissociative effects, elevated blood pressure and bronchodilation. Ketamine is primarily used for the induction and maintenance of general anesthesia. Other uses include sedation in intensive care, analgesia (particularly in emergency medicine and treatment of bronchospasms. Ketamine has also been shown to be efficacious in the treatment of depression (particularly in those who have not responded to other anti-depressant treatment). In patients with major depressive disorders, ketamine has additionally been shown to produce a rapid antidepressant effect, acting within two hours.

The S-ketamine enantiomer (or S-(+)-ketamine or esketamine) has higher potency or affinity for the NMDA reception and thus potentially allowing for lower dosages; and is available for medical use under the brand name KETANEST S.

There remains a need to provide an effective treatment for depression, more particularly treatment resistant depression and/or for the treatment of suicidality, suicidal ideations, and for the prevention of suicide, particularly in the first hours and days after the onset of a major depressive episode.

SUMMARY OF THE INVENTION

The present invention is directed to a method for predicting whether a patient suffering from depression, preferably treatment resistant depression, is genetically predisposed to poorly respond to antidepressants, for example antidepressants which block the reuptake of monoamine neurotransmitters such as serotonin, norepinephrine, dopamine, and the like, comprising genotyping of said patient to determine the patient's genotype at SNP rs4306882 (on chromosome 3).

The present invention is further directed to a method for genotyping a patient to determine the patient's polymorphism at SNP rs4306882, comprising the steps of:
Step A: obtaining a biological sample comprising genetic material of the subject, wherein the subject is undergoing or is to undergo antidepressant pharmacotherapy;
Step B: determining the presence of a G ot T allele at rs4306882.

In an embodiment, the present invention is directed to a method for genotyping further comprising extracting DNA from the biological sample. In an embodiment, the present invention is directed to a method for genotyping wherein the biological sample is a blood sample. In an embodiment, the present invention is directed to a method for genotyping further comprising reporting the determination to the subject, a health care provider, a physician, a pharmacist, a pharmacy benefits manager or an electronic system.

The present invention is directed to a method for the treatment of depression, preferably treatment resistant depression (TRD), comprising:
Step A: genetically testing (or genotyping) a patient suffering from depression (preferably treatment resistant depression) to determine the patient's genotype at SNP rs4306882;
Step B: administering a dosing regimen of ketamine or esketamine, wherein the dosing regimen is adjusted to provide a higher dose and/or greater frequency of the ketamine or esketamine to those patients with a G allele (rather than a T allele) at the polymorphic site of SNP rs4306882.

In an embodiment of the present invention, the methods further comprise genetically testing (or genotyping) the patient suffering from depression, preferably treatment resistant depression, to determine the patient's genotype at one or more of the SNPs as listed in Table 3 which follows herein.

In an embodiment of the present invention, the patient suffering from depression, or in need of treatment for depression, is suffering from treatment resistant depression (TRD).

In an embodiment of the present invention, the dosing regimen comprises administration of esketamine, preferably intranasal esketamine. In an embodiment of the present invention, the esketamine is administered at a therapeutically effective amount. In another embodiment, the esketamine is administered as co-therapy in combination with one or more anti-depressants. In another embodiment of the present invention, the co-therapy is administered in a therapeutically effective amount.

In an embodiment of the present invention, wherein the patient in need of treatment is a patient carrying the G allele at SNP rs4306882, the dosing regimen comprises administration of intranasal esketamine at a dose of between about 28 mg and about 32 mg (preferably 28 mg), at an interval of one to four (preferably one to three, more preferably one to two, more preferably one) times per week, for a period of up to about eight weeks.

In another embodiment of the present invention, wherein the patient in need of treatment is a patient carrying the T allele at SNP rs4306882, the dosing regimen comprises administration of intranasal esketamine at a dose of between about 28 mg and about 32 mg (preferably 32 mg), at an interval of two to five (preferably three to five, more preferably four to five) times per week, for a period of up to about eight weeks.

In an embodiment of the present invention, the dosing regimen is administered for one to eight weeks, preferably for one to six weeks. In another embodiment of the present invention, the dosing regimen is administered for two to eight weeks, preferably for two to six weeks, preferably two to four weeks. In additional embodiments of the present invention, the dosing regimen is administered for one, two, three, four, five, six, seven or eight weeks.

DETAILED DESCRIPTION OF THE INVENTION

The present invention is directed to methods for the treatment of depression, more particularly treatment resistant depression, and/or for the treatment and/or prevention of suicidality (e.g. suicidal ideations) comprising genotyping a patient in need thereof (e.g. suffering from depression, preferably treatment resistant depression) and administering ketamine, preferably esketamine, preferably intranasally, according to a dosing regimen which is selected (preferably optimized) for said patient, based on the patient's genotype at SNP rs4306882, alone or in combination with one or more SNPs, as described in more detail herein.

As used herein, unless otherwise noted, the term "esketamine" shall mean the (S)-enantiomer of ketamine, as its corresponding hydrochloride salt, a compound of formula (I)

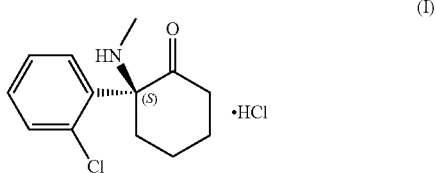

also known as (S)-2-(2-chlorophenyl)-2-(methylamino)cyclohexanone hydrochloride.

As used herein, unless otherwise noted, the term "antidepressant" shall mean any pharmaceutical agent which can be used to treat depression. Suitable examples include, but are not limited to mono-amine oxidase inhibitors such as phenelzine, tranylcypromine, moclobemide, and the like; tricyclics such as imipramine, amitriptyline, desipramine, nortriptyline, doxepin, protriptyline, trimipramine, chlomipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, citolapram, escitalopram, fluvoxamine, and the like; serotonin receptor antagonists such as nefazadone, and the like; serotonin noradrenergic reuptake inhibitors such as venlafaxine, milnacipran, desvenlafaxine, duloxetine and the like; noradrenergic and specific serotonergic agents such as mirtazapine, and the like; noradrenaline reuptake inhibitors such as reboxetine, edivoxetine and the like; atypical antidepressants such as bupropion, and the like; natural products such as Kava-Kava, St. John's Wort, and the like; dietary supplements such as s-adenosylmethionine, and the like; and neuropeptides such as thyrotropin-releasing hormone and the like; compounds targeting neuropeptide receptors such as neurokinin receptor antagonists and the like; and hormones such as triiodothyronine, and the like. Preferably, the antidepressant is selected from the group consisting of fluoxetine, imipramine, bupropion, venlafaxine and sertaline.

Therapeutically effective dosage levels and dosage regimens for antidepressants (for example, mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors, hormones and other pharmaceutical agents disclosed herein), may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) or other sources.

As used herein the term "antipsychotic" includes, but is not limited to:

(a) typical or traditional antipsychotics, such as phenothiazines (e.g., chlorpromazine, thioridazine, fluphenazine, perphenazine, trifluoperazine, levomepromazin), thioxanthenes (e.g., thiothixene, flupentixol), butyrophenones (e.g., haloperidol), dibenzoxazepines (e.g., loxapine), dihydroindolones (e.g., molindone), substituted benzamides (e.g., sulpride, amisulpride), and the like; and (b) atypical antipsychotics, such as paliperidone, clozapine, risperidone, olanzapine, quetiapine, zotepine, ziprasidone, iloperidone, perospirone, blonanserin, sertindole, ORG-5222 (Organon), and the like; and others such as sonepiprazole, aripiprazole, nemonapride, SR-31742 (Sanofi), CX-516 (Cortex), SC-111 (Scotia), NE-100 (Taisho), and the like.

In an embodiment, the "atypical antipsychotic" is selected from the group consisting of aripiprazole, quetiapine, olanzapine, risperidone and paliperidone. In another embodiment, the atypical antipsychotic is selected from the group consisting of aripiprazole, quetiapine, olanzapine and risperidone; preferably, the atypical antipsychotic is selected from the group consisting of aripiprazole, quetiapine and olanzapine.

As used herein, the term "depression" shall be defined to include major depressive disorder, unipolar depression, treatment resistant depression, depression with anxious distress, bipolar depression and dysthymia (also referred to as dysthymic disorder). Preferably, the depression is major depressive disorder, unipolar depression, treatment resistant depression, depression with anxious distress, or bipolar depression. More preferably, the depression is major depressive disorder, unipolar depression, treatment resistant depression and bipolar depression.

As used herein, the term "treatment-refractory or treatment-resistant depression" and the abbreviation "TRD" shall be defined as major depressive disorder that does not respond to adequate courses of at least two antidepressants. One skilled in the art will recognize that the failure to respond to an adequate course of a given antidepressant may be determined retrospectively or prospectively. In an embodiment, at least one of the failures to respond to an adequate course of antidepressant is determined prospectively. In another embodiment, at least two of the failures to respond to an adequate course of antidepressant are determined prospectively. In another embodiment, at least one of the failures to respond to an adequate course of antidepressant is determined retrospectively. In another embodiment, at least two of the failures to respond to an adequate course of antidepressant are determined retrospectively.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (co-morbid) disorders or conditions, genetic testing, and the like.

As used herein, unless otherwise noted, the terms "subject" and "patient" refer to an animal, preferably a mammal, most preferably a human, who has been the object of treatment, observation or experiment. Preferably, the subject or patient has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Wherein the present invention is directed to therapy with a combination of agents, "therapeutically effective amount" shall mean that amount of the combination of agents taken together so that the combined effect elicits the desired biological or medicinal response. For example, the therapeutically effective amount of combination therapy comprising esketamine and a serotonin reuptake inhibitor would be the amount of esketamine and the amount of the serotonin reuptake inhibitor that when taken together or sequentially have a combined effect that is therapeutically effective, more preferably where the combined effect is synergistic. Further, it will be recognized by one skilled in the art that in the case of combination therapy with a therapeutically effect amount, the amount of each component of the combination individually may or may not be therapeutically effective.

Wherein the present invention is directed to the administration of a combination, the compounds may be co-administered simultaneously, sequentially, separately or in a single pharmaceutical composition. Where the compounds are administered separately, the number of dosages of each compound given per day, may not necessarily be the same, e.g. where one compound may have a greater duration of activity, and will therefore, be administered less frequently. Further, the compounds may be administered via the same or different routes of administration, and at the same or different times during the course of the therapy, concurrently in divided or single combination forms. The instant invention is therefore understood as embracing all regimens of simultaneous or alternating treatment and the term "administering" is to be interpreted accordingly.

As used herein, the terms "co-therapy", "combination therapy", "adjunctive treatment", "adjunctive therapy" and "combined treatment" shall mean treatment of a patient in need thereof by administering esketamine in combination with one or more antidepressant(s), and further, optionally in combination with one or more atypical antipsychotics wherein the esketamine and the antidepressant(s) are administered by any suitable means, simultaneously, sequentially, separately or in a single pharmaceutical formulation. Where the esketamine and the antidepressant(s) are administered in separate dosage forms, the number of dosages administered per day for each compound may be the same or different. The esketamine and the antidepressant(s) may be administered via the same or different routes of administration. Examples of suitable methods of administration include, but are not limited to, oral, intravenous (iv), intranasal (in) intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The esketamine and the antidepressant(s) may be administered according to simultaneous or alternating regimens, at the same or different times during the course of the therapy, concurrently in divided or single forms.

Optimal dosages to be administered may be readily determined by those skilled in the art, and will vary with the particular compound or compounds used, the mode of administration, the strength of the preparation and the advancement of the disease condition. In addition, factors associated with the particular patient being treated, including patient's sex, age, weight, diet, time of administration and concomitant diseases, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

EXAMPLES

The following Examples are set forth to aid in the understanding of the invention, and are not intended and should not be construed to limit in any way the invention set forth in the claims which follow thereafter.

Example 1—Retrospective Analysis

We performed a genetic association meta-analysis of treatment resistant depression case control genetic association analyses from two independent cohorts of European ancestry. Irrespective of the definition provided above, in the meta-analysis described in this Example, cases with treatment resistant depression (TRD) were defined as subjects failing two trials of antidepressant treatment regimens and were drawn either from a Cohort J consisting of patients enrolling in antidepressant clinical studies (n=232) genotyped using Ilumina Omni5MExome or from a cohort based on STAR*D study (n=315) genotyped using either Affymetrix 500K or Affymetrix 5.0. Controls were drawn from either the cognitively normal subjects from the ADNI study (n=255) genotyped using Illumina Omni2.5M or the psychiatrically screened healthy controls from NIMH (n=584) genotyped using Affymetrix 500K, respectively. We imputed genotypes based on the reference haplotypes from the 1,000 Genomes prior to meta-analysis to enable direct comparison of variants across the study.

More specifically, for Cohort J, we started with the Illumina Omni5MExome dataset (n~538) comprising subjects from the following studies: (a) RIS-INT-93 (~458 Caucasian subjects including 24 Hispanic subjects); (b) ESKETIV-TRD-2001 (n~26, all races); (c) KETIV-TRD-2002 (n~61, all races). Only the patients meeting TRD criteria were defined as cases and only subjects of European ancestry were included in the analysis leading to this invention. Standard SNP-level and subject-level quality control criteria were applied prior to imputation of sites not directly genotyped. SNP-level quality control criteria included 1) Minor Allele Frequency >1%; 2) SNP-wise genotype missing rate <5%; 3) Hardy-Weinberg Equilibrium p-value >1e-06. Subject-level quality control criteria included 1) subject-wise genotype missing rate <5%; 2) excluded population outliers, cryptic related subject, and subjects with genetically derived gender differing from gender captured in the case report form (CRF) or phenotype file (if exists). The controls for Cohort J were ADNI CN (genotyped using Illumina Omni2.5M, n~281). For the $2^{nd}$ cohort, the Affymetrix 500K Mapping Array/Affymterix 5.0 comprised the STAR*D (n~1851 all races) and NIMH controls (n~1727 all races). Similar case definition criteria and similar quality control criteria were applied. The 2 analysis cohorts matched by genotyping platforms were: 1) Cohort J TRD (Omni2.5M using a subset of markers) vs. ADNI CN (Omni2.5M) and 2) STAR*D TRD vs. NIMH controls screened by Composite International Diagnostic Interview (CIDI-SF) self-report modified to screen for lifetime diagnoses (The Internet-Based MGS-2 Control Samples).

Treatment resistant depression (TRD) was defined as follows: 2 antidepressant failures (1 retrospective and 1 prospective failure for RIS-INT-93; 2 prospective antidepressant failures for STAR*D; or 2 retrospective antidepressant failures for ESKETIV-TRD-2001 & KETIV-TRD-2002). Prospective antidepressant failure was defined by using HAM-D-17 clinical scale for patients with percentage of change in HAM-D-17 score greater than −50%. The minimal treatment length was 6 weeks for RIS-INT-93 and 8-12 weeks for STAR*D.

The associated markers in the meta-analysis (directly genotyped marker P=$8.51 \times 10^{-7}$; imputed marker P=$3.56 \times 10^{-8}$ passing the conventional genome-wide significance threshold (P=$5 \times 10^{-8}$)) were located in a 50 kb interval (3p24.3) in chromosome 3 with only unannotated spliced EST reported, within a linkage interval implicated in a linkage meta-analysis (3p25.3-3p22.1). The genetic data from each TRD sample independently supported this association, with uncorrected significance levels of P=$2.37 \times 10^{-5}$ for the STAR*D cohort and P=0.005 for the Cohort J. (See Table 1 and Table 2, below). Minor allele G was determined to occur at a lower frequency in TRD than in a generally healthy population. Patients with each copy of the G allele had ~0.7× lower odds of exhibiting treatment resistant depression (TRD). rs4306882 was directly genotyped in Cohort J; and imputed in the STAR*D cohort.

TABLE 1

| Cohort | CHR | SNP | BP | A1 | A2 |
|---|---|---|---|---|---|
| Cohort J vs. ADNI CN | 3 | rs 4306882 | 21062584 | G | T |
| STAR*D TRD vs. NIMH Controls | 3 | rs 4306882 | 21062584 | G | T |

| Cohort | FRQ | INFO | OR | SE | P |
|---|---|---|---|---|---|
| Cohort J vs. ADNI CN | 0.386 | 0.9777 | 0.6754 | 0.14 | 0.005078 |
| STAR*D TRD vs. NIMH Controls | 0.3771 | 1.0139 | 0.5249 | 0.1525 | 2.37E−05 |

Abbreviations in Table 1 are as follows:
  CHR Chromosome code, if map file specified
  SNP SNP code
  BP Base-pair position, if map file specified
  A1 Allele 1 code
  A2 Allele 2 code
  FRQ Frequency of A1, from dosage data
  INFO R-squared quality metric/information content
  OR Odds ratio for association
  SE Standard error of effect estimate
  P p-value for association tests

TABLE 2

| For Chromosome 3, SNP rs4306882 at Base pair position 21062587 | | | | | | |
|---|---|---|---|---|---|---|
| A1 | F A | F U | A2 | CHISQ | P | OR |
| G | 0.3378 | 0.4321 | T | 10.16 | 1.43E−03 | 0.6703 |

Abbreviations in Table 2 are as follows:
  A1 Minor allele name (based on whole sample)
  F_A Frequency of this allele in cases
  F_U Frequency of this allele in controls
  A2 Major allele name
  CHISQ Basic allelic test chi-square (1df)
  P Asymptotic p-value for this test
  OR Estimated odds ratio (for A1, i.e. A2 is reference)
The sequence ID for SNP rs4306882 is as follows:

```
SEQ. ID. 1:
GGATGCCACA TGCAGATGTA TTTTCTTTGG TCCACATATG

GCATCCAACC CATGAGCTAT AGAAAATATG GATTTCTGGA

TTTCTTTGAA ACACTGAAAG ATCTGGAGCC TCTGGGCCAC

TGTTACTGGA TAATAGCAAC AGCCTGAGTG TTTGCATTTA

TAACCTGTAA TAAGAGACGC ATGTCTCCTT GCTGCTCAAG

TTATAGATCT GACAGCCCAG GATATGATTA ATCAGAGCTC

AGGGCTCAGG AAGCCATTCT CCACATCTGG CAGAGCCCGA

CAAAATCTTT GCAATCAGAT TAACGAAGCA GTGACATGAT

GTTCTATTAG TGGGGCATG GACATGCAAA ATCATTATGC

AGAACAATTC ATTATCATAG CTGACCATGT ACAGGGTTTT

AGCTGCATGT CGATGTGGCA CAGCTCACTG AAGATGCATG
```

```
GATAAACGCT GTGGCTAAGG CATTGTGAGA GCAATTGGTA

GGAGCTAGAA AGCTAGCTCT

K

AAGCCAAGCT AGAAGAGAAA CACAGTTCTG GGATCACCAT

TCATTTTGCT CTTTCTGGGT CCTTTTATAT CTGCTTTAGC

AAGGTACCTG CTTTAACAAT GTACATTCTT GCATGAATGT

TTTCTTTTCT CTTTCAATTC TTCTTCCATC CTGGTGTTTA

GGATATCACT GGGGTGGGAT AGTGGGAGAG GTGGCAGTTT

TATTTTGTTT TTAAGTATAT CAGTTCTCCT TTTTGATATC

AGCTTTTCTT TTTGAATAGT CCAGGATATA CTTGCCTCTC

AAGCAGCTTT TTTTTTTCTC AAAGCCAGTT CTTCTTATGC

AACAGACTTA CTATATCATT CACAGATTGT ACCATGAGGG

TTCACTTTCT TGCACCTATA TTAGGCCACA ACCTCTAAGC

ACAAAGGTCT TTTCATGACT GTTTATTGAA ATACCCAGCA

AGAATTTTCA TCAGACAGAG TTTTAGTCAT GCTTTAACTC

TGCAACTTAT TAAAATGGGA

>gnl|dbSNP|rs4306882|allelePos = 501|
totalLen = 1001|taxid = 9606|snpclass = 1|
alleles = 'G/T'|mol = Genomic|build = 138
```

SNP rs4306882 was further determined to be in linkage disequilibrium (LD) with an array of the SNPs in the close by genomics region as shown in Table 3, below.

In certain embodiments, the present invention is directed to methods (as described herein) wherein the patient's genotype is determined at any single SNP listed in Table 3 below, alone or in combination with a determination of the patient's genotype at SNP rs4306822. In certain embodiments, the present invention is directed to methods (as described herein) wherein the patient's genotype is determined at any subset of SNPs selected from the list in Table 3 below, alone or in combination with a determination of the patient's genotype at SNP rs4306822.

TABLE 3

| BP | SNP | A1 | A2 | N | P | P(R) | OR | OR(R) | Q | I |
|---|---|---|---|---|---|---|---|---|---|---|
| Chromosome 2 (CHR) | | | | | | | | | | |
| 119536884 | rs1551133 | C | A | 2 | 2.85E−07 | 1.68E−04 | 0.4418 | 0.4392 | 0.1699 | 46.91 |
| Chromosome 3 (CHR) | | | | | | | | | | |
| 21061286 | rs869495 | G | A | 2 | 5.54E−07 | 0.0006712 | 0.5941 | 0.5898 | 0.1367 | 54.84 |
| 21061473 | rs869494 | T | A | 2 | 6.68E−07 | 0.001478 | 0.5967 | 0.5914 | 0.1129 | 60.21 |
| 21062584 | rs4306882 | G | T | 2 | 8.51E−07 | 4.85E−05 | 0.6019 | 0.5997 | 0.2233 | 32.57 |
| 21063058 | rs4465961 | T | C | 2 | 8.85E−07 | 0.000537 | 0.5939 | 0.5897 | 0.1513 | 51.43 |
| 21063578 | rs7625772 | T | G | 2 | 6.24E−07 | 0.00096 | 0.5947 | 0.5897 | 0.1263 | 57.21 |
| 21063804 | rs7633632 | G | A | 2 | 6.21E−07 | 5.14E−06 | 0.5963 | 0.5954 | 0.2733 | 16.68 |
| 21063919 | rs7612422 | C | G | 2 | 1.43E−07 | 1.64E−07 | 0.5804 | 0.5803 | 0.3149 | 1 |
| 21067747 | rs7646153 | G | C | 2 | 8.42E−07 | 0.0004885 | 0.5984 | 0.5947 | 0.1539 | 50.81 |
| 21069166 | rs1391144 | G | A | 2 | 9.95E−07 | 9.95E−07 | 0.6022 | 0.6022 | 0.3234 | 0 |
| 21072614 | rs2047387 | G | A | 2 | 2.04E−07 | 2.04E−07 | 0.5822 | 0.5822 | 0.3415 | 0 |
| 21077201 | rs6769146 | G | A | 2 | 4.83E−07 | 4.83E−07 | 0.5911 | 0.5911 | 0.3302 | 0 |
| 21077685 | rs6550565 | T | A | 2 | 7.97E−07 | 6.70E−06 | 0.5866 | 0.5856 | 0.272 | 17.12 |
| 21081507 | rs56871503 | C | T | 2 | 6.99E−07 | 0.0004664 | 0.5965 | 0.593 | 0.1525 | 51.14 |
| 21085039 | rs11295121 | TG | T | 2 | 9.11E−07 | 9.11E−07 | 0.6007 | 0.6007 | 0.3262 | 0 |
| 21087408 | rs4858288 | A | G | 2 | 3.76E−07 | 3.76E−07 | 0.5893 | 0.5893 | 0.3634 | 0 |
| 21088048 | rs1391138 | G | T | 2 | 2.82E−07 | 2.82E−07 | 0.5852 | 0.5852 | 0.3252 | 0 |
| 21088878 | rs9881998 | C | T | 2 | 5.63E−07 | 3.08E−05 | 0.5918 | 0.59 | 0.228 | 31.2 |
| 21089069 | rs9811079 | G | A | 2 | 2.62E−07 | 2.62E−07 | 0.5843 | 0.5843 | 0.3787 | 0 |
| 21093953 | rs13097458 | C | A | 2 | 9.97E−07 | 9.97E−07 | 0.597 | 0.597 | 0.389 | 0 |
| 21097393 | rs973870 | C | A | 2 | 6.85E−07 | 0.0004483 | 0.5957 | 0.5918 | 0.1531 | 51.01 |
| 21099489 | rs7652147 | G | A | 2 | 7.14E−07 | 0.0004306 | 0.5958 | 0.5921 | 0.1551 | 50.52 |
| 21099939 | rs141786492 | TTTTC | T | 2 | 4.54E−07 | 0.0008831 | 0.5822 | 0.5771 | 0.1245 | 57.63 |
| 21100108 | rs7644744 | A | G | 2 | 6.62E−07 | 0.000343 | 0.5943 | 0.5908 | 0.1612 | 49.05 |
| 21102620 | rs985536 | G | A | 2 | 6.54E−07 | 6.54E−07 | 0.5921 | 0.5921 | 0.4025 | 0 |
| 21106260 | rs9865061 | T | A | 2 | 2.28E−07 | 8.84E−05 | 0.58 | 0.5773 | 0.184 | 43.35 |
| 21106404 | rs11128983 | G | A | 2 | 5.11E−07 | 5.42E−05 | 0.589 | 0.5868 | 0.211 | 36.07 |
| 21107235 | rs9850499 | C | T | 2 | 3.45E−07 | 2.87E−05 | 0.5798 | 0.5779 | 0.221 | 33.23 |
| 21107330 | rs71935600 | CAG | C | 2 | 2.39E−07 | 0.0001414 | 0.5709 | 0.5676 | 0.1714 | 46.55 |
| 21108963 | rs200621794 | AAAG | A | 2 | 3.56E−08 | 3.56E−08 | 0.5581 | 0.5581 | 0.3527 | 0 |
| 21108964 | rs67575809 | AAG | A | 2 | 2.80E−08 | 2.51E−07 | 0.5549 | 0.5546 | 0.2812 | 13.9 |
| 21109078 | rs7372757 | G | A | 2 | 2.25E−07 | 2.25E−07 | 0.5801 | 0.5801 | 0.7251 | 0 |
| Chromosome 4 (CHR) | | | | | | | | | | |
| 148693230 | rs2164527 | C | T | 2 | 4.17E−07 | 4.17E−07 | 0.451 | 0.451 | 0.6757 | 0 |
| Chromosome 11 (CHR) | | | | | | | | | | |
| 86572384 | rs12285365 | G | A | 2 | 4.43E−07 | 4.43E−07 | 0.5116 | 0.5116 | 0.6906 | 0 |

Abbreviations in Table 3 above, are as follows:
CHR Chromosome code, if map file specified
BP Base-pair position, if map file specified
SNP SNP code
A1 Allele 1 code
A2 Allele 2 code
N Number of valid studies for the SNP
P p-value for association tests
P(R) Random-effectsmeta-analysis p-value
OR Odds ratio for association
OR(R) Random effects OR estimate
Q p-value for Cochrane's Q stratistic
I I² heterogeneity index (0-100)

Thus, we believe that we have identified a candidate genetic marker for TRD with association p-value passing genome wide significance using a relatively small sample size by GWAS standard. The identification of genetic markers associated with resistance to biogenic amine-based antidepressant drugs holds the potential to guide researchers toward unprecedented targets in the discovery of novel treatments for TRD.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method for treatment of depression comprising:
    Step A) obtaining a biological sample comprising genetic material from a patient suffering from depression;
    Step B) detecting the patients genotype at rs4306882 by performing a genotyping assay on the genetic material from Step A;
    Step C) detecting a G allele at the polymorphic site of rs4306882 in the patients genetic material; and
    Step D) administering esketamine intranasally at a dosage of about 28 mg to about 32 mg, one to three times per week for up to eight weeks to said patient.

2. The method as in claim 1, wherein the depression is treatment resistant depression (TRD).

3. The method of claim 2 wherein the patient with treatment resistant depression is administered esketamine in co-therapy in combination with a therapeutically effective amount of at least one antidepressant.

4. A method for treatment of depression comprising:
    Step A) obtaining a biological sample comprising genetic material from a patient suffering from depression;
    Step B) detecting the patients genotype at rs4306882 by performing a genotyping assay on the genetic material from Step A;
    Step C) detecting a T allele at the polymorphic site of rs4306882 in the patients genetic material; and
    Step D) administering esketamine intranasally at a dosage of about 28 mg to about 32 mg, four to five times per week for up to eight weeks to said patient.

5. The method of claim 4, wherein the depression is treatment resistant depression (TRD).

6. The method of claim 5, wherein the patient with treatment resistant depression is administered esketamine in co-therapy in combination with a therapeutically effective amount of at least one antidepressant.

* * * * *

SEQUENCE LISTING

<160> NUMBER OF SEQ ID NOS: 35

<210> SEQ ID NO 1
<211> LENGTH: 1001
<212> TYPE: DNA
<213> ORGANISM: Homo sapiens

<400> SEQUENCE: 1

```
ggatgccaca tgcagatgta ttttctttgg tccacatatg gcatccaacc catgagctat      60
agaaaatatg gatttctgga tttctttgaa acactgaaag atctggagcc tctgggccac     120
tgttactgga taatagcaac agcctgagtg tttgcattta taacctgtaa taagagacgc     180
atgtctcctt gctgctcaag ttatagatct gacagcccag gatatgatta atcagagctc     240
agggctcagg aagccattct ccacatctgg cagagcccga caaaatcttt gcaatcagat     300
taacgaagca gtgacatgat gttctattag tgggggcatg gacatgcaaa atcattatgc     360
agaacaattc attatcatag ctgaccatgt acagggtttt agctgcatgt cgatgtggca     420
cagctcactg aagatgcatg gataaacgct gtggctaagg cattgtgaga gcaattggta     480
ggagctagaa agctagctct kaagccaagc tagaagagaa acacagttct gggatcacca     540
ttcattttgc tctttctggg tccttttata tctgctttag caaggtacct gctttaacaa     600
tgtacattct tgcatgaatg ttttcttttc tctttcaatt cttcttccat cctggtgttt     660
aggatatcac tggggtggga tagtgggaga ggtggcagtt ttattttgtt tttaagtata     720
tcagttctcc tttttgatat cagcttttct ttttgaatag tccaggatat acttgcctct     780
caagcagctt ttttttttct caaagccagt tcttcttatg caacagactt actatatcat     840
tcacagattg taccatgagg gttcactttc ttgcacctat attaggccac aacctctaag     900
cacaaaggtc ttttcatgac tgtttattga aatacccagc aagaattttc atcagacaga     960
gttttagtca tgctttaact ctgcaactta ttaaaatggg a                        1001
```

<210> SEQ ID NO 2
<211> LENGTH: 601
<212> TYPE: DNA
<213> ORGANISM: Homo sapiens

<400> SEQUENCE: 2

```
tagattttc aaactttatt atttcttagg atgtgtatag ttggttattt tgcttaacta       60
ctttaactat tgataaatta atctgtaaaa aaagaaaga ttttatcgtt catgtttatc      120
tctggatttt tgtgagcaac ttaaagatg aaggtgaaa ggtaaaggt tttgaaatat        180 tgtgatgaat tatcataatt aaagtttata tcgttagtaa gaactaaaag tatatgtcta     240
tgcaccctaa ctcataatat gtactattca cagtctatat atacacaaag aaaaacaaac    300
```

```
mattactaaa tgccaattac atgccaacct tactggaagc tcttagcacc cattaactca    360
tttaatccta agaacaatcc attgttttaa gtatgattta tttcttcaaa ttatagatgg    420
taaaactaac cctaaacatg ttgcagcata aacagttgcc taatttatta cttttagaaa    480
accatgacac caagatttaa tcccacttat tttatgaaag tcattgaaac agaaaccaat    540
ttctcaataa taccctcata aacatatgac tttgaaatac tctaaaaata ttctagtttt    600
t                                                                   601
```

<210> SEQ ID NO 3
<211> LENGTH: 1103
<212> TYPE: DNA
<213> ORGANISM: Homo sapiens

<400> SEQUENCE: 3

```
atgaccagca actaccagaa gctacaggag tggcatgcaa cagactaccc ttacaacctc     60
agaaggagca aaccctatca acatcttgat tttggccttc tcgcctccag aattgtgaca    120
gaacaaatta ttgttatttt aagccattca gtttgtcatc ttttgttaca gcagccctag    180
acagtcaggg tatgctgaac agctgtaacc aacacaccca agatgtgtaa tggctccaac    240
acaaccaaag tttacagtaa cagtccaagg ccaagttcca ttggtgggca cctctactgc    300
acacggtcat ttagacatcc aagctaacag agggtttgcc atctttaaca gtggtttccc    360
aagactgcct tggtcctacc attctagtcc atgggaacag aaaacagaag aggtttgata    420
agctggccaa aaatggctat atcacttctg gtcacatttt cttgaagaga acttagtaat    480
atggctctac tcagttgcaa tagggacata tgcaatatgg tgcagctgga ggagagctag    540
tgattcttct gmaatgatga agctgctat ttgaaaaggg ggcagtgaga gagcttattt    600
ccaggaatgc aaaagccagg gagttagaga aacagtgtcc aactcttcca ccagtcttga    660
ggataatgca atttaagaga tggatcaggt gaaggctttt gaaaaaaaga atagaaaact    720
agggcaaagc aagggcccta ggaagatggc aagcatcctg caaggtttag ctattagaaa    780
actcatggga atgccctatt attatatcca gatgttctaa ggaaatttca acccaactct    840
gccccaaggc ataggctcca gaaagaatca tcctgcttac agcaccaggc ctctgattca    900
aagaacttga gagagaataa aattagcaca gcatagccag aactgaagtc ctgtaaggac    960
ccccataaag tagacatcag gacccgagag attcatcaaa ggagacccag tttgttaatt   1020
ggtttcctgg taaacagtca agaacctggg tttggtggat tcaggagtca gatagagctg   1080
ggaataaatc ctcctttatg gct                                           1103
```

<210> SEQ ID NO 4
<211> LENGTH: 1001
<212> TYPE: DNA
<213> ORGANISM: Homo sapiens

<400> SEQUENCE: 4

```
tctgttccct ggtgactgtt tctgctctcc tgaccactgc acatctgtga catctgctca     60
gctaaagtta gtggcttcta tctgttgcct ggttctagac ttcgtgtttg gcttcaactt    120
atgctttgtt tctaaaatct caaatctcct gggttttac ttctagccct gttctctacg    180
gttcaagacc agcccagctg atattcagct aaaaataaca ttgtgtaaca catagtttat    240
tacataactt agtatttaat agtcaatgct aattgaatac agaaaagtga gatttaaatg    300
cggtttagat aacacactgg tagacaaacc cagaagaggg gagcagaatt tatgtacaat    360
```

```
atgactcttt atatgtttgt ttttctttca aattatgata agttctcatc aatgtaaaag    420
gccattattt tactgtttgt agtggtttca gcatctctga ggtgggaaac agtgggtact    480
gctgcttgaa aatgaaagaa ytaagtgctc actgtgcacc tcactctgtg aagaacttt    540 atagactttt ttcatggagt acctcaaaca aaggaagta ctgatacttg aaaacatta     600 gtcgtaagat gatatagatg cttctaatta accataggaa tcaaattatc tatcattttc    660 ttgagttttct acattgtgct aggccttcta ctaagaacta taaagatgac attaataact   720
tacaataatt tccaagatag gttttagaat tttagtctat cacagttaat ggaattggga    780
cctagaaaac tcacatagag tgtagtgaat ccaggattta atcaaagcca agttagagag    840
gttccttata ccatagaggc tccaaggata ccacctacct ttcaggtcac ataacttcag    900
aaggaactga actaactaaa gtgagccttg attaaagccc ataataaaca gaggtttgag    960
gtaaatgcag aaatttcaag taagagaaga aactaattgt t                      1001
```

<210> SEQ ID NO 5
<211> LENGTH: 1001
<212> TYPE: DNA
<213> ORGANISM: Homo sapiens

<400> SEQUENCE: 5

```
ttcccttttct ataggtaagc aaaatttaat ttacagaggt gaagtgatct gtttataatt    60
gtatacctag ggagtagaaa agactaaatg ctgatctaag ccctaggact tatggtcatt    120
tcagcaaccc taaagttctc ataaacttcc ttctatgtta atacaacttg tttgtcttct    180
aatgtcatct gttccctggt gactgtttct gctctcctga ccactgcaca tctgtgacat    240
ctgctcagct aaagttagtg gcttctatct gttgcctggt tctagacttc gtgtttggct    300
tcaacttatg ctttgtttct aaaatctcaa atctcctggg ttttttacttc tagcccctgtt   360 ctctacggtt caagaccagc ccagctgata ttcagctaaa aataacattg tgtaacacat    420
agtttattac ataacttagt atttaatagt caatgctaat tgaatacaga aaagtgagat    480
ttaaatgcgg tttagataac wcactggtag acaaacccag aagaggggag cagaatttat    540
gtacaatatg actctttata tgtttgtttt tctttcaaat tatgataagt tctcatcaat    600
gtaaaaggcc attattttac tgtttgtagt ggtttcagca tctctgaggt gggaaacagt    660
gggtactgct gcttgaaaat gaagaacta agtgctcact gtgcacctca ctctgtggaa    720
gaactttata gactttttc atggagtacc tcaaacaaaa ggaagtactg atacttggaa    780
aacattagtc gtaagatgat atagatgctt ctaattaacc ataggaatca aattatctat    840
cattttcttg agtttctaca ttgtgctagg ccttctacta agaactataa agatgacatt    900
aataacttac aataatttcc aagataggtt ttagaatttt agtctatcac agttaatgga    960
attgggacct agaaaactca catagagtgt agtgaatcca g                      1001
```

<210> SEQ ID NO 6
<211> LENGTH: 1001
<212> TYPE: DNA
<213> ORGANISM: Homo sapiens

<400> SEQUENCE: 6

```
ttggtaggag ctagaaagct agctctgaag ccaagctaga agagaaacac agttctggga    60
tcaccattca ttttgctctt tctgggtcct tttatatctg ctttagcaag gtacctgctt    120
taacaatgta cattcttgca tgaatgtttt cttttctctt tcaattcttc ttccatcctg    180
gtgtttagga tatcactggg gtgggatagt gggagaggtg gcagttttat tttgtttta    240
```

```
agtatatcag ttctcctttt tgatatcagc ttttcttttt gaatagtcca ggatatactt      300
gcctctcaag cagctttttt ttttctcaaa gccagttctt cttatgcaac agacttacta      360
tatcattcac agattgtacc atgagggttc actttcttgc acctatatta ggccacaacc      420
tctaagcaca aaggtctttt catgactgtt tattgaaata cccagcaaga atttcatca       480
gacagagttt tagtcatgct ytaactctgc aacttattaa aatgggagca ctttatataa      540
tttgcttaac tcttctaagc tttagttcct tcttcctaaa aataggagtt gtaggaagaa      600
agatgagtgg gtcctgtttc atttggttac ttttacatta aaatgcaatg aatctctatg      660
ggtactctga acttgtgact ggctaggtaa gccagatttc agtgtgcttc acagacctgg      720
tgaccttgga cttggaaggg agaaggacac aagatgtctc actgaggcct tttggagtaa      780
gctattctcc aatatacatt tcttacagga tgcttgtcta cttactcatt tggtcactat      840
ccttaagtgc atagctcttt ataggaaaca atttcaatag tggaagagaa acgataagtt      900
tcattcacat acaaaacctc aactcaacca atcaatgttt ataaagcaca ctcatcgtct      960
ttgaaaaaag atatcagtgt cacaggtcag gttccccaga a                         1001

<210> SEQ ID NO 7
<211> LENGTH: 1001
<212> TYPE: DNA
<213> ORGANISM: Homo sapiens

<400> SEQUENCE: 7
aatgggagca ctttatataa tttgcttaac tcttctaagc tttagttcct tcttcctaaa       60
aataggagtt gtaggaagaa agatgagtgg gtcctgtttc atttggttac ttttacatta      120
aaatgcaatg aatctctatg ggtactctga acttgtgact ggctaggtaa gccagatttc      180
agtgtgcttc acagacctgg tgaccttgga cttggaaggg agaaggacac aagatgtctc      240
actgaggcct tttggagtaa gctattctcc aatatacatt tcttacagga tgcttgtcta      300
cttactcatt tggtcactat ccttaagtgc atagctcttt ataggaaaca atttcaatag      360
tggaagagaa acgataagtt tcattcacat acaaaacctc aactcaacca atcaatgttt      420
ataaagcaca ctcatcgtct ttgaaaaaag atatcagtgt cacaggtcag gttccccaga      480
aagtgcactc tgaagtaaaa kctcatatat ggtaagttta ttaagaaatg ctcttcagat      540
caatactctt ggaataaaaa ggaaggaatc aggattatga agaaaagctt tggctgtgat      600
gcaatctcaa cacaattttt acccaatccc acagataaaa atagctggga ttactgttta      660
gagtgggtga agagcaagcc tttatactcc acactgacaa gttgttaatt gtggctacct      720
ctaagaggaa gagtcctcct taaagaggca actctatcta gcccatggca atttgaagtg      780
tgggtgggaa ccgagaagct aaataaatca attttttgct tttcctcagt acagatattt      840
cccctttttga agccacctag agcattgcgt gtaccactta cttttgcatg atgctttata      900
tttcacaaac attatctcac atgcctccca tgatctttca tgaagcagat aaagcacata      960
ttatttagag aataagaaac aaaacttttc agactttttcc c                        1001

<210> SEQ ID NO 8
<211> LENGTH: 1001
<212> TYPE: DNA
<213> ORGANISM: Homo sapiens

<400> SEQUENCE: 8
acacaagatg tctcactgag gccttttgga gtaagctatt ctccaatata catttcttac       60
```

| | |
|---|---|
| aggatgcttg tctacttact catttggtca ctatccttaa gtgcatagct ctttatagga | 120 |
| aacaatttca atagtggaag agaaacgata agtttcattc acatacaaaa cctcaactca | 180 |
| accaatcaat gtttataaag cacactcatc gtctttgaaa aagatatca gtgtcacagg | 240 |
| tcaggttccc cagaaagtgc actctgaagt aaaatctcat atatggtaag tttattaaga | 300 |
| aatgctcttc agatcaatac tcttggaata aaaggaagg aatcaggatt atgaagaaaa | 360 |
| gctttggctg tgatgcaatc tcaacacaat ttttacccaa tcccacagat aaaaatagct | 420 |
| gggattactg tttagagtgg gtgaagagca agcctttata ctccacactg acaagttgtt | 480 |
| aattgtggct acctctaaga rgaagagtcc tccttaaaga ggcaactcta tctagcccat | 540 |
| ggcaatttga agtgtgggtg ggaaccgaga agctaaataa atcaattttt tgcttttcct | 600 |
| cagtacagat atttcccctt ttgaagccac ctagagcatt gcgtgtacca cttacttttg | 660 |
| catgatgctt tatatttcac aaacattatc tcacatgcct cccatgatct ttcatgaagc | 720 |
| agataaagca catattattt agagaataag aaacaaaact tttcagactt ttcccaatga | 780 |
| ttgggaaaag tagcctttaa caaataaaaa tctctgccgg acttagcttt cttttaaaca | 840 |
| aaataggggt gtaaaataac ttacctgcct actatttaat cccagcacta ggatctatga | 900 |
| atgtgtacct tgcacagatt tatgtgtttg ctaagtggag gagacagcca cagcatctgt | 960 |
| atcctgtgga ctactgttcc agggctctat acactgcccc a | 1001 |

<210> SEQ ID NO 9
<211> LENGTH: 1001
<212> TYPE: DNA
<213> ORGANISM: Homo sapiens

<400> SEQUENCE: 9

| | |
|---|---|
| taggaaacaa tttcaatagt ggaagagaaa cgataagttt cattcacata caaaacctca | 60 |
| actcaaccaa tcaatgttta taaagcacac tcatcgtctt tgaaaaaaga tatcagtgtc | 120 |
| acaggtcagg ttccccagaa agtgcactct gaagtaaaat ctcatatatg gtaagtttat | 180 |
| taagaaatgc tcttcagatc aatactcttg gaataaaaag gaaggaatca ggattatgaa | 240 |
| gaaaagcttt ggctgtgatg caatctcaac acaatttta cccaatccca cagataaaaa | 300 |
| tagctgggat tactgtttag agtgggtgaa gagcaagcct ttatactcca cactgacaag | 360 |
| ttgttaattg tggctacctc taagaggaag agtcctcctt aaagaggcaa ctctatctag | 420 |
| cccatggcaa tttgaagtgt gggtgggaac cgagaagcta aataaatcaa ttttttgctt | 480 |
| ttcctcagta cagatatttc ccttttgaa gccacctaga gcattgcgtg taccacttac | 540 |
| ttttgcatga tgctttatat ttcacaaaca ttatctcaca tgcctcccat gatctttcat | 600 |
| gaagcagata aagcacatat tatttagaga ataagaaaca aaacttttca gacttttccc | 660 |
| aatgattggg aaaagtagcc tttaacaaat aaaaatctct gccggactta gctttctttt | 720 |
| aaacaaaata ggggtgtaaa ataacttacc tgcctactat ttaatcccag cactaggatc | 780 |
| tatgaatgtg taccttgcac agatttatgt gtttgctaag tggaggagac agccacagca | 840 |
| tctgtatcct gtggactact gttccagggc tctatacact gccccacact accctgatag | 900 |
| cactgaggtc aatgatgggt ctattgcctg agactgtaga aaagacaagc acaaaagcat | 960 |
| gtgaaagaac aaggatacaa tctgagggaa tgtttccaga g | 1001 |

<210> SEQ ID NO 10
<211> LENGTH: 1614
<212> TYPE: DNA
<213> ORGANISM: Homo sapiens

<400> SEQUENCE: 10

```
acctcttatg tctttaattt cctcctttca agttttattt gccagaccat attctccttt      60
taaatgttag aaatgtaaat gttaaaatgc cttccattcc atatacttta agtaggtgat     120
ttcatctgac ccttaaattt cctctcttat caattcctcg atgattcatc tgagctttct     180
tgctgatgtc tcctgaaaat agatgtccag cccgagtttt acaagcctac tccatatttg     240
tatatctacc cacctaataa atatattcac ttgaatgtct aatgcacatt ttaaacttaa     300
catgaccaaa atcgattttt ttcctaaaat tccactccat ccatagcctt gctcaactca     360
gttaatagca attcaatatt ttcaattggg gtaattcttg actccccacc tctcaaacca     420
cattgtccag tctctcaaat ccaattgctt gtaacttcag aataaatcta taacatgatc     480
gtatctcgcc aactccatgg ctactgtctt agtcttaagc accataattg ctgaaaatta     540
ttgcaatagc ttcctaattg gttttttctgc ttctaccgaa gttatttaag cagctgtgcc     600
agttttttctg agacctacca ggttttatca ctgaaagtca tgtgtctcag aaaacccctc     660
attctcaaga aaactgggac atctgctatg tactctcaag acaacatgta gagttgttgt     720
ttaaaaatat atcaaaccat atcactcttc taatscaatc cttcattgat tccctacttc     780
actcagggta aaaactaaca tccttacaat ggccttcaag accatattca atgtagtcac     840
tgtttcctct gcttgtctga cttctataac tctccttctc agtttctagc cacggtgact     900
tatactgttt gagcccaggt gcccttctcc tttggggtct ttgcactggt tcttccctct     960
gggactctca ccctctagat atatacatgg ctcacacctc atttatttca gagcttttct    1020
catacttcaa cttctcaatt atcctcattc tggccatctt aaatagtatt acaatgtcca    1080
ctctcagaac tctgaatcct cagtgtattc ccaatattca gaacagttcc tagctcaata    1140
aatattgagt acctaatatt tgttaaataa acaaatgaat ggcttcattt cccatccaca    1200
tatatggtgt gttttctctc tctccctccg aatatatctc ccttttgttt tattttcctc    1260
atgattgaga ttggtgccct tataaacaag actgcagaga gctagtcccc tttactgttt    1320
gaggacatct ggctagatgg tgacatctat gagaaagggg gacctcacca gccactgaat    1380
ctcccagcga cttcctattg gacatcccag cctccagaac tgtgagaaat aaaatgctat    1440
tatgagttac ccagcctata gtattttgtt atagcattcc aaatgggcta agatatatat    1500
gtgtgtgtgt gtgtgtgtgt gcgtgtgtgt gtgtgtatgt attccaaatg gactaagata    1560
tgtaaaagtg tgtgtgcata tgtgtatgtg tattccatgt gtagatggta aatg           1614
```

<210> SEQ ID NO 11
<211> LENGTH: 1001
<212> TYPE: DNA
<213> ORGANISM: Homo sapiens

<400> SEQUENCE: 11

```
ttatagcaat tcaaatggac taagatatgt gtgtatataa aagcatgtgt acatgtgtat      60
atgtgtgtgt gtgtgtgtgt accccacgtg tagatggtaa ataaagctct tcttatgttt     120
attatatata cagtcgtgca tcacttaaca acaagtgtat gttgagaatg tatttttagg     180
ctatttcact gttccacaaa cttcataggg tgcacttaac acaaaccttg actacatagc     240
ctactataca cctaggataa atggcatagc ctattgctcc taggctacaa acctgtacag     300
tacaccatgt tactgtactg taggtaattg taacaagatg gtgtttgtgt atctaaacat     360
atctaaacat agaaaaggtt aaaatatggt attataattt tatgaaactg ccattatata     420
```

```
tgaagtttat tcttgatcaa acattgtta tgcagtgcat gtattatatg tatgtataag      480
gtatatatgg tatataatgt dtatgtatat atggtatatt ttatatatgt ttatacatac      540
accgagagaa gatatataca tgtgtggggg tatatgtaaa tacctcctcc tatgcagaca      600
tctcttaaca gttcacatat ctaagtattt ctgccttctt aactctacca ccagggcatc      660
ctattggcat ttcagactcg atttattcaa aatttagttc attgtctttc taagaaagcc      720
acactttctc cagaatgact atattttatg tctaattaca caaggtagga atttgaattc      780
cacatattat accccttct ccatgatttt ctttatctgc aatcctacca cttctgaata       840
tatggaatct ctttacttcc ctccacctat gttattatcc atgaccacag tattatttct      900
cagcaggagg ctgttcctaa ctgactttca cattttctct ctctcctctc ttaaatccat      960
ttttcaccct gaggtaagct ggaacacaaa aatataattg t                          1001
```

<210> SEQ ID NO 12
<211> LENGTH: 1001
<212> TYPE: DNA
<213> ORGANISM: Homo sapiens

<400> SEQUENCE: 12

```
gagttactgt gttttcttg aagcaaacaa agatttgaga atgtagacta tgtgtgctgg       60
gggctccatg tccttttcga tttctttatg cattcttgag tagaaaaaag cagagtgctt      120 gtgtttttt tctagttaat tctggctctg atctgtgaca tcctctgaat ttaggaagaa       180
gccatctttt atcccactta tggcacctca ggttcacatt gctggtccag atgcaaaaca      240
cagtcaatct ttgattatc cccaaacata actcacataa agcattatta tataaaatag       300
aatttactga agattttttt gtaatgctga atgtgtgctt ttcatgttaa acatttatgt      360
tgaagacaca ttgtttatta gtagttgggt gtttttaga gtctctgaaa tttctgtgga      420
catagtctct agcctctgct ctacctttcc ctctcttctc tgctctccat cccttttccaa     480 gtttctattt cttatctaga rcaatttagc tttcttctct ttcttatttt cctctcatct     540
ctgtttatac aaaaatattc ttttaattat ggatgattct tagctatttt ttgataccag      600
gtattaaata ttggtatgtt tttgtattat tttgttttgt cttgctgtat gtgtctaaca     660
atatgcattt tcctagatca gaaccattca gtataaatat aatgtgagtc atatgtttac     720
ttttgcattt tctaatagtc acattaatga attaaaaaaa ctcaggtata acaaacatta     780
attgtatatt ttatttaacc aagtaagttt aaaatattat ctcaagatgc aaccaatata    840
aaaattattg agatatttaa tcttttttcat tgtactaagt cttttataatc tggtgtgtat    900 tttataccctc cagcccatct gaattcagat gctaaatttt cattggatat gcttgatctc    960
tctttagatt tcataaaatt tgtagtggaa ttattagact t                          1001
```

<210> SEQ ID NO 13
<211> LENGTH: 4205
<212> TYPE: DNA
<213> ORGANISM: Homo sapiens

<400> SEQUENCE: 13

```
ataaaattaa tagcgttaaa tgctcatgat gtgccattac gtggactta acaatatttt       60 gatgacatta cacttcacat aacatccttc ctaaaagaca aaattattaa ttagataata     120
gctttaaatt ttaaaactag ataaactaac cccttcccc agtaggtttt gttattttag      180
aattgtgcag ggcttagta ttttttcatc ttatttttt aattgacaga taaaaattgt       240
gtatatttgg tgtaaataag atgttttgaa atacatatac attctggaat ggctagatca     300
```

```
acttaattaa catatgcagt acctcacaaa catcatttat ttgaggcaaa taaaatccat    360
tctgttagaa ttttcaagtg taagcacatt gctgttaact ttaatcactg tgttgcacaa    420
tagatctcct agattcatcc atgttatcat aaatgacaga attttcttct ttttaaggct    480
gaataatagt gcatatgcgt atatatgtat gtataaataa aacgttttca ctatccgttc    540
atccattgat agacacttag gttgattcta gaatatgcca caatggacaa tggagtacag    600
ctgtctctac agatggattt tctttctttg gctatatacc aagaaatgaa atgtctagat    660
catgtggtaa ttctgttttt taatttttt acaactcttc ctaacagttt tccataatag     720
ctgtactaat ttacatttcc acaaacaatg tacaagaatt cccttcctc tacatcctaa     780 tacttgttat cttttgtttt tctgataaca gccattctga aggtgtgag gtaatgtctc     840 attgtagttt tgatttgaat tccctgacga ttagtggttt taagcatttt tcatatacca    900
ttggccattt gtatgtcttg agaaacatct attaagatcc tttgccagta ttttaattag    960
attattttcc ttgctattga attctttaag atctttattt tttttgtgta tacatagata   1020
catatattat taacgttgat tatttatctg taaatttatt tttataattt caacttttat   1080
tataggttaa agactacacc tgcaggtttg ttgcatgagt aaattcctga ttctgaggct   1140
tggagttaca atgatcccat tactcaggca gtgagaatat tacccaacac gtagatcttc   1200
aaggcatgca cccctccctc gttcccttgt ctagtggtcc ctggggtcta ttgttcccat   1260
ttttatgttc atgtgtattc aatatatagc tcccacttac aggtgagaac atgcagtatt   1320
tggtttcctg tttttacgtt agttcactta aaataatgcc ttccagctcc aaccatgttg   1380
ctggaaagga tatggctttg tttttattta tggctgtata gtattccctg gtgtatatgt   1440
accacgtttt ctttacccaa tccactgctg atgggcacct aggtggattc caggtccttg   1500
atattgtgaa tagcactgca ataaacctac agatgcgtgt gtgttttga ttgaatgaac    1560 aattttcctt tgagtatata cccagtagtg gggttgctgg attgagtcgt agctatattt   1620
taagatcttt gagaactctt cacattttgc atattaactc tattatatat gtggtttgca   1680 aatattttt tcatacagta gattgtctct tcactccgtt gattttttaa attgtatagt    1740
acctttgttt taatgtaatc ttatgtgtcc attttcttc actttgtttt attttagtag    1800
ttatacagtt tcaggtctta tgctttaaat ctttttatcca atttgagttt atttttatac   1860
atggtgtgag ataaagatcc aatttttctt ttctccctct ctgtcgccag gctggattgt   1920
aatggcgcaa tcttggctca ctgcaacctt ggcctcctgg gttcaagtga ttctcctggc   1980
tcagcctcct gagtagctgg gattacaggc acccgccacc acacccagat aattttgta    2040 tttttagtag agatggggtt tcaccaggtt ggccaggctg gtctcgaact cctgacctca   2100
ggtgatccac ccgccttggc ctcccaaagt gctgagatta caagtgtgag ccaccgtgcc   2160 tgacccccaat tttattctac atatacatat acatatccag ttctgccaac accacttgtt   2220
gaagagactc ccctttctgc attgtgtaat tttggcatct ttgtcaaaaa tcaattgatg   2280
gtaaatggat gaatttattt ctaggctcta tattctgttc cattggtgta gatatctgtt   2340
tttaggccaa tacaatgctg ttccaaagac tatagctttg tagtagattt taaagtcagg   2400
tagtatgatg cctctagctt tgttcttttt gttaaagatt gctttggcta ttagtgtctt   2460
gtggttccrt gtgaatttta ggattttctt cctatttctg tgaaaaatgc tactggaatt   2520
ttgagagaga atcaatctgt agatctcatt acatagtgaa atattttaac aatccatgga   2580
catagaatat ttttctgtct atatttgtgt cttcttcagt ttctttcatc aaagttgtat   2640
```

-continued

```
agttttggtg tgtagactct tcgccttctt ggtaaaattt attcctaagt atttatttat    2700
ttattttat ttatttattt ttttgagatg gagtcttgct ctgtcaccca ggctggagtg     2760
cagtggtgcg atctcagctc actgcaacct ccacctcctg ggttcacacc attctcctgc    2820
ctcagcctcc caagtagctg ggactacagg cgcccgccac cacacttggc taatttttg     2880
tatttttta gtagagatgg ggtttcacca tgttagccag gatggtctcg atcccctgac     2940
ctctggatcc gcgaaccttg gcctcccaaa gtgctgggat tacaggcgtg agccactgca    3000
cctggccctt attcctcagt attttatgtt tgttttgttt gttttgtttt ggggttttt     3060
ttagctattg taagttgatt tttctgattt cttttttgga aagttcattg ttagtgtatg    3120
gaaactctac tgattttgt atgttaattt ttgtatcctg caactttcca gactttaaat     3180
tagttctaat agatttagtt agtgtcttta gagttctaga tggtaagatt atattgtctg    3240
cagagacaat ttaattattt tcttctgatt tagatgcctt taaatctttc tcttgcctaa    3300
ttgctgtggc taaaacttgc tgtattatgt tgcataaaag tgagaggagt gggcatcctg    3360
gtcttgttcc tgatcttaga gaaagagctt tcaggcttt accattgagt ataatgttag     3420
ctgtggcctg tcatacatgg cctttattat gttgagttat actacccca taccaaatat     3480
gttgagagtt tttatcatga aaatgtgctt ttcagtgcat taaattttaa ttaccatatc    3540
tattttcaa actagaaaag cgatttgctt aaattaatta aaataata atacatattt       3600
taatccattt atcaattaca atttacatag gtactgttgt aactgctgct gtttgcataa    3660
aatactcaaa taaaaatact acaatcttaa atcagtacat agtgaaatat cattcaaact    3720
gaatcaatcc atagacacca actagattgg tgaacagctt atgtgtaata ctagaaatga    3780
ttagtgttcc caacatgtgc agtaaaatac aataataata tctcacatga tgcaatagtt    3840
aaagtgaaat atagctctat caaaataata aagttgtgta acacaaatgt attttatact    3900
gcttaggttt taaaatttga ataaattaaa attaaataaa atgaaatgtt aagtttttg     3960
ctagccacat tcagatgttc aatagccaaa tatgactagt ggctaccgta ttagataaaa    4020
cagttctaga ttctacattg gtgtttgtta atgtttcaca ctctcagtgt ttcctaatgt    4080
tcaacatgtc tctttctcct gctttttttt aaattatagt ttctaattct tcctatctag    4140
cacattgcct gaatgtcagt gaatattatg taaatgaata aataaacaac cctatacttt    4200
gccac                                                                4205
```

<210> SEQ ID NO 14
<211> LENGTH: 4205
<212> TYPE: DNA
<213> ORGANISM: Homo sapiens

<400> SEQUENCE: 14

```
ataaaattaa tagcgttaaa tgctcatgat gtgccattac gtggacttta acaatatttt      60
gatgacatta cacttcacat aacatccttc ctaaaagaca aaattattaa ttagataata     120
gctttaaatt ttaaaactag ataaactaac cccttccccc agtaggtttt gttatttag      180
aattgtgcag ggcttagta ttttttcatc ttattttttt aattgacaga taaaaattgt      240
gtatatttgg tgtaaataag atgttttgaa atacatatac attctggaat ggctagatca    300
acttaattaa catatgcagt acctcacaaa catcatttat ttgaggcaaa taaaatccat    360
tctgttagaa ttttcaagtg taagcacatt gctgttaact ttaatcactg tgttgcacaa    420
tagatctcct agattcatcc atgttatcat aaatgacaga attttcttct ttttaaggct    480
gaataatagt gcatatgcgt atatatgtat gtataaataa aacgttttca ctatccgttc    540
```

```
atccattgat agacacttag gttgattcta gaatatgcca caatggacaa tggagtacag    600
ctgtctctac agatggattt tctttctttg gctatatacc aagaaatgaa atgtctagat    660
catgtggtaa ttctgttttt taattttttt acaactcttc ctaacagttt tccataatag    720
ctgtactaat ttacatttcc acaaacaatg tacaagaatt ccctttcctc tacatcctaa    780
tacttgttat cttttgtttt tctgataaca gccattctga aaggtgtgag gtaatgtctc    840
attgtagttt tgatttgaat tccctgacga ttagtggttt taagcatttt tcatatacca    900
ttggccattt gtatgtcttg agaaacatct attaagatcc tttgccagta ttttaattag    960
attattttcc ttgctattga attctttaag atctttattt tttttgtgta tacatagata   1020
catatattat taacgttgat tatttatctg taaatttatt tttataattt caacttttat   1080
tataggttaa agactacacc tgcaggtttg ttgcatgagt aaattcctga ttctgaggct   1140
tggagttaca atgatcccat tactcaggca gtgagaatat tacccaacac gtagatcttc   1200
aaggcatgca cccctccctc gttcccttgt ctagtggtcc ctggggtcta ttgttcccat   1260
ttttatgttc atgtgtattc aatatatagc tcccacttac aggtgagaac atgcagtatt   1320
tggtttcctg tttttacgtt agttcactta aaataatgcc ttccagctcc aaccatgttg   1380
ctggaaagga tatggctttg tttttattta tggctgtata gtattccctg tgtatatgt    1440 accacgtttt ctttacccaa tccactgctg atgggcacct aggtggattc caggtccttg   1500
atattgtgaa tagcactgca ataaacctac agatgcgtgt gtgttttga ttgaatgaac    1560 aattttcctt tgagtatata cccagtagtg gggttgctgg attgagtcgt agctatattt   1620
taagatcttt gagaactctt cacattttgc atattaactc tattatatat gtggtttgca   1680 aatattttt tcatacagta gattgtctct tcactccgtt gatttttaa attgtatagt     1740 acctttgttt taatgtaatc ttatgtgtcc attttctct actttgtttt attttagtag    1800
ttatacagtt tcaggtctta tgctttaaat cttttatcca atttgagttt attttttatac  1860 atggtgtgag ataaagatcc aatttttcttc ttctccctct ctgtcgccag gctggattgt   1920
aatggcgcaa tcttggctca ctgcaacctt ggcctcctgg gttcaagtga ttctcctggc   1980
tcagcctcct gagtagctgg gattacaggc acccgccacc acacccagat aatttttgta   2040
tttttagtag agatggggtt tcaccaggtt ggccaggctg gtctcgaact cctgacctca   2100
ggtgatccac ccgccttggc ctcccaaagt gctgagatta caagtgtgag ccaccgtgcc   2160 tgacccaat tttattctac atatacatat acatatccag ttctgccaac accacttgtt    2220
gaagagactc ccctttctgc attgtgtaat tttggcatct ttgtcaaaaa tcaattgatg   2280
gtaaatggat gaatttattt ctaggctcta tattctgttc cattggtgta gatatctgtt   2340
tttaggccaa tacaatgctg ttccaaagac tatagctttg tagtagattt taagtcagg    2400 tagtatgatg cctctagctt tgttcttttt gttaaagatt gctttggcta ttagtgtctt   2460
gtggttccgt gtgaattta ggattttctt cctatttctg tgaaaaatgc tactggaatt    2520
ttgagagaga atcaatctgt agatctcatt acatagtgaa atattttaac aatccatgga   2580
catagaatat ttttctgtct atatttgtgt cttcttcagt ttctttcatc aaagttgtat   2640
agttttggtg tgtagactct tcgccttctt ggtaaaattt attcctaagt atttatttat   2700
ttatttttat ttatttattt ttttgagatg gagtcttgct ctgtcaccca ggctggagtg   2760
cagtggtgcg atctcagctc actgcaacct ccacctcctg ggttcacacc attctcctgc   2820
ctcagcctcc caagtagctg ggactacagg cgcccgccac cacacttggc taattttttg   2880
```

```
tatttttttta gtagagatgg ggtttcacca tgttagccag gatggtctcg atccctgac     2940 ctctggatcc gcsaaccttg gcctcccaaa gtgctgggat tacaggcgtg agccactgca    3000
cctggccctt attcctcagt attttatgtt tgttttgttt gttttgtttt ggggttttt     3060 ttagctattg taagttgatt tttctgattt cttttttgga aagttcattg ttagtgtatg    3120
gaaactctac tgattttttgt atgttaattt ttgtatcctg caactttcca gactttaaat   3180
tagttctaat agatttagtt agtgtcttta gagttctaga tggtaagatt atattgtctg    3240
cagagacaat ttaattattt tcttctgatt tagatgcctt taaatctttc tcttgcctaa    3300
ttgctgtggc taaaacttgc tgtattatgt tgcataaaag tgagaggagt gggcatcctg    3360
gtcttgttcc tgatcttaga gaaagagctt tcaggctttt accattgagt ataatgttag    3420
ctgtggcctg tcatacatgg cctttattat gttgagttat actacccta taccaaatat     3480 gttgagagtt tttatcatga aaatgtgctt ttcagtgcat taaattttaa ttaccatatc    3540 tattttcaa actagaaaag cgatttgctt aaattaatta taaaataata atacatattt     3600
taatccattt atcaattaca atttacatag gtactgttgt aactgctgct gtttgcataa    3660
aatactcaaa taaaaatact acaatcttaa atcagtacat agtgaaatat cattcaaact    3720
gaatcaatcc atagacacca actagattgg tgaacagctt atgtgtaata ctagaaatga    3780
ttagtgttcc caacatgtgc agtaaaatac aataataata tctcacatga tgcaatagtt    3840
aaagtgaaat atagctctat caaaataata aagttgtgta acacaaatgt attttatact    3900
gcttaggttt taaaatttga ataaattaaa attaaataaa atgaaatgtt aagttttttg    3960
ctagccacat tcagatgttc aatagccaaa tatgactagt ggctaccgta ttagatagaa    4020
cagttctaga ttctacattg gtgtttgtta atgtttcaca ctctcagtgt ttcctaatgt    4080
tcaacatgtc tctttctcct gctttttttt aaattatagt ttctaattct tcctatctag    4140
cacattgcct gaatgtcagt gaatattatg taaatgaata aataaacaac cctatacttt    4200
gccac                                                                4205

<210> SEQ ID NO 15
<211> LENGTH: 1001
<212> TYPE: DNA
<213> ORGANISM: Homo sapiens

<400> SEQUENCE: 15
aataaaacct ctttcgctcc cattgtcacc gaaggacctg acaacctgtc tttctacact       60
tcgcctacaa tcagtgtcct tcacccttaa ctctgtctct ttccctttat attaggttat      120
agtgggctct ctattaccaa gcccagtgga atcatttttgt cctttattac ctctctgtgt    180
catctttaag agaaatacat atatatttct ctctacgtag aatggccatc tgtttcttca     240
tcacctgagg aatcattcaa tatgactttc aaatgaatat tcagagaatt ttctaatgta    300
gaaacatagg tattcatcta aaatcatttc aaaaaccatc tccctttatt taagaatgtt    360
attctcttct acagaaaagc ctctagtgtt tactggggag atttgtgctg tgggaagaag    420
gggacagtgc tgaactgcac acaacctaac aaatcaatcc tgataattag tagagtggca    480
gatggggagc ccagccatgc ycacaccttt ctgagaacca gctcaattcc tatctctgct    540
ctgacacatt cttgcaggta gttagccact ctctgtgagt ttttttgca ctctgttcat     600 agttccatta aagaacttgt tatatagctt tctagtcctt tgttgacata tctactaaaa    660
tgtgaatttc ttaagggcaa gtccatttta tctttatatt tctgcatata tagttttattc   720 taagctcatt tattttgaac gaataaattt ggggaggaga caacaaagta tgagagatat    780
```

| | | | |
|---|---|---|---|
| gtttaaaacc | tataaatgca | aaaccttgaa tggaaagctt | gttcttgata gtttttaagt | 840 |
| tcttggatga | tgtatttcta | gagggtagac agtacctgcc | aaggcataaa ttttttaataa | 900 |
| agggctcatt | tttttaaagag | atctttaaaa tatcgccgtt | tcttaggtct gtgcattgag | 960 |
| atttcagttt | atctgtaaca | gaactactta tttaggaacc | t | 1001 |

<210> SEQ ID NO 16
<211> LENGTH: 1001
<212> TYPE: DNA
<213> ORGANISM: Homo sapiens
<220> FEATURE:
<221> NAME/KEY: modified_base
<222> LOCATION: (501)..(501)
<223> OTHER INFORMATION: a, c, t, g, unknown or other

<400> SEQUENCE: 16

| | | | |
|---|---|---|---|
| accctgttac | cagaaaggag | tcctaattct gaccccaaga | gaaggtcctt aaatctcgtg | 60 |
| caagaaagat | ttcagggtaa | gtccacggag taaagtgaaa | gcaagtttat taagaattaa | 120 |
| aggaataaaa | gaatggttac | tccataggca gagcagcccc | aagggctgct ggttggctat | 180 |
| ttttatggtt | atttcttgat | tatatgctaa acaaacaaaa | atggattatt catgagtttt | 240 |
| ctgggaaagg | ggtgggtgat | tcctggaact gagagttcct | cccatttcca gaccatatag | 300 |
| ggtaacttcc | tgacgtttat | aaactgtcat ggtgctggta | ggagtgtctt ttagtatgca | 360 |
| aattcattac | aattagagta | taatgagcag tgaggatgac | caggggtcac tttcttcaca | 420 |
| atcttggttt | tggtgggatt | tggccatttt ctttacctcc | tgctgttcta tcagcaaggt | 480 |
| ctttgtgacc | tgtatcttgt | ngctgacctc ctgtcttatc | ctgtgagtta aatgcctaa | 540 |
| cctttttggga | ctgcagccca | gtaggtctca gtcttatttt | actgagcacc tattccagat | 600 |
| ggagtagatc | tggttcaaat | gccactgaca acccaaacat | tttttttaaaa tgtttagaca | 660 |
| tacaaaagga | gacaggtaga | catataaaag gaaattccaa | taacttggtc tccaacttaa | 720 |
| agtaagtatg | tctttattga | acactcatgt gattggaaat | gtggaagggc ttttaatgta | 780 |
| ttatttaatt | attttaacac | ctaaaagggg ttggtaccat | tagtcactcc cattttacag | 840 |
| atgagaaagc | tgagactgag | aaaatgaatt acctggccta | gatgtcaaaa caagaaggtt | 900 |
| gactttgaga | gccattgctt | ttattaagtg taatattagg | ttatcttta aaaactcaag | 960 |
| ttagggagaa | ctgaaagtct | tcaaagagag taaataactc | c | 1001 |

<210> SEQ ID NO 17
<211> LENGTH: 1001
<212> TYPE: DNA
<213> ORGANISM: Homo sapiens

<400> SEQUENCE: 17

| | | | |
|---|---|---|---|
| ttatcctagt | tttacctgta | ttatcatgtt taatctttaa | atagccctct tatgaaggca | 60 |
| tcagcattac | ttaccttcac | ttttaaaatt agaaaattaa | aaccagaagg agttaagcaa | 120 |
| cacacatgag | atcatacagc | agttggatat tagggatggg | gtttgaaccc aagaatttta | 180 |
| tcacccaagc | ccccttttaga | ctactgcatt acatagcctg | gcatacaaag ccaatgaagt | 240 |
| aaaatatgta | ctattaaatt | aaatgatgag gagtcccgta | ccagcagtat aactccaata | 300 |
| tgagtaagga | catgattaaa | acaagttaca aaatagggac | atatatggaa aagtatttga | 360 |
| tgtctatggg | atggaaaaga | gttaatacct tttccatata | aatgtatttt aagataaata | 420 |
| ataaaatgat | agacacacat | tacaatagac aaaggcaaaa | aataagcatg cttagtggcc | 480 |

| aataataggt ttagactctg rtaattaaac aaatgcaact caaaatctga atgaaatgct | 540 |
| aatttaacct atcgaaataa caaattaatt ttaaaaatta attttaaaaa ataatttaaa | 600 |
| gttttgaaga ctgtatgggg aaaatgacac attcataccc atacaatagt tgtattacac | 660 |
| ttatgcaaag aatgacagaa taaaagaaac atatagtaag cagaaatgca actatttata | 720 |
| ttaaatgaaa acataaaatg ccagtgacta ggggtataat taaataggct gtaaaagtag | 780 |
| acataactag aactcaaaat ctgagatcag ccttgtagat atagaagtaa agacattgtt | 840 |
| cttccccaaa aacttgtgag gtatattctc taagacctaa aatatgtttc ccattcaaaa | 900 |
| attcatatat atatgaatat gcatatatta tatgtttatt gcatatataa ttttcatgc | 960 |
| aatgttgtac tgttataagt tttaaaatat caggcctaca t | 1001 |

<210> SEQ ID NO 18
<211> LENGTH: 1001
<212> TYPE: DNA
<213> ORGANISM: Homo sapiens

<400> SEQUENCE: 18

| tttattaaat gaatgtacaa atgaatagag agtacctttt caaaaataca gttcaatgac | 60 |
| tatccataaa aggcaaagaa agcaatcaga ctctccccat caaatttta aaaaaccact | 120 |
| ttgttacatt ccgtaaccaa cattctgtga gccttagagc aatttaaagt cattatgcct | 180 |
| cagtttccta gtatttaaaa cagtgaatat tacgtttgct ttgtttacac cattatgaca | 240 |
| atcaaatttg aaaacatgca ttaaagccct ttaagaaagc atataagtgc gcttccgtgg | 300 |
| tgagaaagaa aatatctgca aataagggga tttgatatct gaactgagaa aatatagctc | 360 |
| tttctaggta atgtttgagc tgacaagtga gtacatttga atgatttaat ggacacttaa | 420 |
| aagtttcttt tcattctaaa tcatatgaag gattcaatta gactttcatc ttaaaacagt | 480 |
| aatgcaatta cttctatgat maaacaacat ttttaaaaag tgacaacata cacttttagc | 540 |
| ttcaaatttg ttctctgtcc cttcaagctt attctatcac tatataaaac taagcaatgt | 600 |
| aatacagaac aattctcaat agccaggtaa cttatatttg atgtaggcct gatattttaa | 660 |
| aacttataac agtacaacat tgcatgaaaa attatatatg caataaacat ataatatatg | 720 |
| catattcata tatatatgaa ttttgaatg ggaaacatat tttaggtctt agagaatata | 780 |
| cctcacaagt ttttgggaaa gaacaatgtc tttacttcta tatctacaag gctgatctca | 840 |
| gattttgagt tctagttatg tctactttta cagcctattt aattataccc ctagtcactg | 900 |
| gcatttatg ttttcattta atataaatag ttgcatttct gcttactata tgtttctttt | 960 |
| attctgtcat tctttgcata agtgtaatac aactattgta t | 1001 |

<210> SEQ ID NO 19
<211> LENGTH: 1001
<212> TYPE: DNA
<213> ORGANISM: Homo sapiens

<400> SEQUENCE: 19

| gactttaaat tgctctaagg ctcacagaat gttggttacg gaatgtaaca aagtggtttt | 60 |
| ttaaaaattt gatggggaga gtctgattgc tttctttgcc ttttatggat agtcattgaa | 120 |
| ctgtattttt gaaaaggtac tctctattca tttgtacatt catttaataa ataacttgct | 180 |
| ttaaattcta ttaggacaat ttgaccttc ttttccttc ctactttctc gacaaagttg | 240 |
| cctctctgaa caagtgtttg tcatcatata tctgaccccc agcccctact ctgcaggaac | 300 |
| agatgaaaca ccctgtgaat ctctcaacac tatgttgtcc aacacaaata taatgtgagg | 360 |

```
cctctatgta atttaaactt cctagtagcc gcatttttta aaatagaaaa aaaaggtaaa      420
attaatttta ttagtgcatt ttattcaatc taatattcta acttacaata atataaacat      480
tattaatgag atattttgta yttttttggt acaaagtctt tgatatccca tgtatatttt      540
atacttacac acattcaatt tgaactaatt acactaaaag tgctcaatag ctatatgatt      600
gaacagtgca gtctgagggc aattgggact tcttattgac tattttgact cttggttaaa      660
taaaattgaa ataatttcag actttaagtg ggcagttagg aatatatctg ctttcaaagt      720
taccaaggaa gctctgctag ttaactttat tctcatactc tattattttt catacattaa      780
aatgtgaact tcttttaatt gactctgtgg tttgttgttg ttgttttttgt ttttctcctc      840 actttgttct gaccttcttc ttttcctttt cagtaagatt tgtcctgtct ccacaaggac      900
caggcttaga ataggaatag taaatgacct atctggagag taaagaaatg ttcctcttcc      960
cctcaaattc cttttctctt attgaggcct gatttccaca g                        1001

<210> SEQ ID NO 20
<211> LENGTH: 1001
<212> TYPE: DNA
<213> ORGANISM: Homo sapiens

<400> SEQUENCE: 20
taggacaatt tgacctttct tttcctttcc tactttctcg acaaagttgc ctctctgaac       60
aagtgtttgt catcatatat ctgaccccca gcccctactc tgcaggaaca gatgaaacac      120
cctgtgaatc tctcaacact atgttgtcca acacaaatat aatgtgaggc ctctatgtaa      180
tttaaacttc ctagtagccg catttttaa aatagaaaaa aaggtaaaa ttaatttttat       240 tagtgcattt tattcaatct aatattctaa cttacaataa tataaacatt attaatgaga      300
tattttgtac ttttttggta caaagtcttt gatatcccat gtatattta tacttacaca       360 cattcaattt gaactaatta cactaaaagt gctcaatagc tatatgattg aacagtgcag      420
tctgagggca attgggactt cttattgact attttgactc ttggttaaat aaaattgaaa      480
taatttcaga ctttaagtgg rcagttagga atatatctgc tttcaaagtt accaaggaag      540
ctctgctagt taactttatt ctcatactct attattttc acattaaa atgtgaactt        600 cttttaattg actctgtggt tgttgttgt tgttttgtt tttctcctca ctttgttctg       660
accttcttct tttcctttc agtaagattt gtcctgtctc acaaggacc aggcttagaa       720 taggaatagt aaatgaccta tctggagagt aaagaaatgt tcctcttccc ctcaaattcc      780
ttttctctta ttgaggcctg atttccacag gagtctcttc atttctttc tttattatgt      840 tattagtctg ctaacttcaa taatagataa attccaaatt tcagtttcta acccccaaat      900
ctacttctct ctcagatagt atgccaaatt caggcttatt ttcagcaagg actccggcat      960 ggggatttg agggtggggt ttctattcca caaagtcatt c                         1001

<210> SEQ ID NO 21
<211> LENGTH: 1001
<212> TYPE: DNA
<213> ORGANISM: Homo sapiens

<400> SEQUENCE: 21
catacaataa taagggggaga ctttaacacc ccaccaacag tattagacag atcatcaagg      60
cagaaaatta acagatattc aggatctgaa ttcaacgctt gaccaaattg acttaataaa      120
ctccctattc aagaaatggt gctgggataa ctgaatagcc acgtgcagaa gattgaaact      180
```

| | |
|---|---|
| ggacccttc cttacataat atacaaaaat taactcaaat ggattaaaga cttaaattta | 240 |
| aatcctaaaa ctatgaacaa cctggaggat aacctaggaa gtataattct ggacatagga | 300 |
| tctggcaaag atctcatggt gaagaaacca aatgcaattg caataaaaac aaaaattgac | 360 |
| aactgggacc taaataaact aaagagcttc tgcacagcaa aataaactat caaagagta | 420 |
| aacagacaat ctacagaatg ggagaaaata tttgcaaact atgcatctga caaggtcta | 480 |
| atatccaaca tctatgagga mtttaaacaa atacacaagg aaaaaaaaaa caaccccatt | 540 |
| aaaaagtgag caaggacat aacagacac ttttcaaaaa aagacatata tgcggtcagc | 600 |
| cagcatgtga aaaatgtgc aacatcacta atcattagag aaatgcaaat taaaactaca | 660 |
| attcgatact gtctcacacc agtcagaatg gctgctctta aaagtcaat aataacaga | 720 |
| cactagtgag gttgcaaaga aaacccctta tacacttctg gtgggaatgt aaattagttc | 780 |
| aaccattgtg gaaagcaatt tggtgatttc tcaaagaact caaagcagaa ttaccattca | 840 |
| acccagcaat ccattattgg gtatatccca aaggaatata aggtcttcta tcataaatac | 900 |
| acatgcacat gtatatccat tgcagcacta ttcacaatag caaagacatg gaatcaacct | 960 |
| aaatgcctat aaagagtagg ctgaataaag aaaatttggt g | 1001 |

<210> SEQ ID NO 22
<211> LENGTH: 1001
<212> TYPE: DNA
<213> ORGANISM: Homo sapiens

<400> SEQUENCE: 22

| | |
|---|---|
| aagtcatttt aaaaatctta aaaagccaaa gagaacctgg gaaatctaga tgagcacatg | 60 |
| tatatttgtt gaacaattgc tccaggtata tggaatttat ggtctaggat agaatgtgaa | 120 |
| aatgtggaca aatagctaca atacaaagca taattaactt agtgtcacaa ttgatagcta | 180 |
| cacacagcaa catgagcatt caaggaaaag gggaaatcaa tccaaatgga actactgagt | 240 |
| tcagtagatt ggcccataat actctatcct ggcttcctat ctcttacctc ccgccacaaa | 300 |
| ttctgcacca gaacaatctc agtttctcac ttagcgctgt ttgctctttt atttcccctt | 360 |
| ctgtgccttt cagaggctac ttctgcttag aattttctct tccattgagc acttgttcaa | 420 |
| ttttcattaa tgttgtaaaa ctcattcaag taaaaattcc tcaatgaaat catctctgat | 480 |
| tgaccaggag agatctagct ktcctctctt ttgttcctcc atggaatttt acttgctctt | 540 |
| gttttgccct aagaattaag cacgtcaaat ggcacatcaa gggagctaac gtataccttt | 600 |
| gaacattgcc ctcaggcatt tattcttagg catattttgg ccttatttat tttatattgt | 660 |
| tataattata ctctaaatac agttgcatat ccaagcatct tttacagtta accttgatac | 720 |
| aataaggctt taattacata attctaaaat attatatcat attccaatga gagcctgcac | 780 |
| cagttgactt ctccacatct ttttggctaa acacaattgt tttctatttt tcataaataa | 840 |
| cagaccaaca tgtgttttgg gatccctaa gggcaggtaa tcatgaatct cattgactta | 900 |
| ttttatgtca aagagggat actaaactat tccttatttt ctcactagca ttactggata | 960 |
| gaaattttct tctgggttac taaatgacct ctaagagttg a | 1001 |

<210> SEQ ID NO 23
<211> LENGTH: 1001
<212> TYPE: DNA
<213> ORGANISM: Homo sapiens

<400> SEQUENCE: 23

| | |
|---|---|
| gagtctgaat gtctatatgg tatgtatatg atacaatttt tgtaaagctt aaaaataagc | 60 |

```
ataaatgata ttctatttag aaagagctta tggggtaaag ttgtttaaat aaattatgga      120
ataacaaacg taaaatttta gatagaaatt gcctctgagg gaacgtaagg ggatataact      180
aggcaatagt agcatatgat tttcactgga atttggtagt attttggttg ttaagttggg      240
tggtgggttc gtgaatgttc aattaatcac tataattcac aatttccata ctaactacat      300
aaagttttga tcatattaag tgaatatatt ttttataatt cagaggtaaa caactacttc      360
taaagtataa agagccagca agatataatg aactctgaag aaattttaga gttcactgac      420
taaaaaaaaa atgtattgtc tatatgtgtt ttatttgaat ttcaatgtcc ctacaaagat      480
aaggagactc tgtggcagat rgatctgaag atgatacctg gcgatttcct attcccagtg      540
tgcatggctt tgggtattcc ccacctctgg agtatgggtg agaactgtga cttgctttta      600
atcaattaaa tatgagagtt cacttccaca gttagtgtag attacatggc aaaaaagatg      660
gagtgtcact cttgtgatga taaatgtgac tcgtgcctca gcctcccaag tggctgggat      720
tacaggcgtg cgccaccaag ccctgctaat atttatagat atagtatttt tagtagagac      780
aggattttgc tgttttggcc agactggctt gaactcccgg cctcaagtga tttgcccgcc      840
tcggcctccc aaggtgctgg gatttcaggc ttgagccact gtgtccagcc tcaaatctct      900
attttagagt tgttattaac ctttgtgaaa cagagaactg tagcctttct ttttctttct      960
ttctttcttt ctttcttttt tctttctttc tttctttctt t                          1001

<210> SEQ ID NO 24
<211> LENGTH: 101
<212> TYPE: DNA
<213> ORGANISM: Homo sapiens
<220> FEATURE:
<221> NAME/KEY: modified_base
<222> LOCATION: (51)..(51)
<223> OTHER INFORMATION: a, c, t, g, unknown or other

<400> SEQUENCE: 24
ttttagagtt gttattaacc tttgtgaaac agagaactgt agcctttctt ntttctttct       60
ttctttcttt cttttttctt tctttctttc tttctttctt t                          101

<210> SEQ ID NO 25
<211> LENGTH: 1001
<212> TYPE: DNA
<213> ORGANISM: Homo sapiens

<400> SEQUENCE: 25
tcacttccac agttagtgta gattacatgg caaaaaagat ggagtgtcac tcttgtgatg       60
ataaatgtga ctcgtgcctc agcctcccaa gtggctggga ttacaggcgt gcgccaccaa      120
gccctgctaa tatttataga tatagtattt ttagtagaga caggattttg ctgttttggc      180
cagactggct tgaactcccg gcctcaagtg atttgcccgc ctcggcctcc caaggtgctg      240
ggatttcagg cttgagccac tgtgtccagc ctcaaatctc tattttagag ttgttattaa      300
cctttgtgaa acagagaact gtagcctttc tttttctttc tttctttctt tctttctttt      360
ttctttcttt ctttctttct ttctttcttt ctttctttct ttctttcttt ctttcttctt      420
tctttctttt cttctttctt tctttcctct ttttctttct тттттттttcg atggggttg      480 gggagacaga ttgagagagc rcgagagcga gagattatgc acatttgtga gctctttaaa      540
actagctcaa gaaagatcct cagaagacca acatcctaga aatcagtacc aaacacaact      600
agtgtaacat aaatagcttc ctttcttaaa aacagctatt tgaagaaagt tagctgtcaa      660
```

```
tcaaaaacag ttttatttga tcagacagag gcaagatgct atggctgttt agccaaagaa      720
aatgacatta tagatacatg taaaattcca acacattgtg taatgtaaca aaacttaagc      780
tgtcttctca ttattattgt tattaattta gatctatatt ctactgactt aggtgagaaa      840
attctccact taccgctttg aaagttaacc aactttctat ggattgttca tttgtttaat      900
agtacaagca atgaaaacat gttttaccat aggtcttaag tatgtagcac cttcctccac      960
cagtatttaa tcatagacct tatactaagg catacaattt t                         1001
```

<210> SEQ ID NO 26
<211> LENGTH: 1001
<212> TYPE: DNA
<213> ORGANISM: Homo sapiens

<400> SEQUENCE: 26

```
acattattat tctaaactag ttattcagta attaaaagga ggaaaagact gctttcaaaa       60
ggtataggta tttgtgaagg catttttgaga ggtgttaact ctacttaaat ataaatacat     120
accattttga aagttatgag cttcaccata gggaaattca tgttctttga tttagaaact     180
atactcctag ggatatttgt ccaaggacat ttaggagaag gaaaagaac atggacaact      240 atttattgaa ctcttactac attctagtta gtacttccca ataaacgtt ctgtaacgtt      300 gtaagtgttc tttacctgct gtagaatatg gtagccacat gtgaccattg agtatttgaa    360
atgtagtatg caaccgagga tttaaatctt taatttatt taatttttat taactcaaac    420
ttaaatttaa gtagccatgt gtggtatcat attggactgc acagtgagac acatgttaag   480
caatttacag aaattacatt ycttaattat tattatgatc tttctattaa ttttattcta   540
cagatatgaa aactgtagga aattaaataa cctgcaaagg tcaccaactt tgaaagtggt   600
atattgaaat ttgaggccag gtagtgtgat gctgtagctc gtgttctgct aggctacttc    660
tctatgcata ttgacttcca atgataggaa aattgttgca tacacttgaa cctaacatga    720
ggtaaaaacc tatgatacta ttgagtgaaa attgttacaa caatttgcag aaggaaatgc    780
ctttatgaca aattaaaata gaagaatgca aaagaatata gactttaaaa gtataattat    840
atgcaaataa tatgagcaag ttgatagtaa tatacaaatt tgaacataaa ttcttttttca   900 gtgataaaat tatggataaa tctcaagagt ctttagtgct gtcttttact aggtttaatt    960 ttgttttttgt tgattgttct tcggattaaa tataacaatg a                       1001
```

<210> SEQ ID NO 27
<211> LENGTH: 1001
<212> TYPE: DNA
<213> ORGANISM: Homo sapiens

<400> SEQUENCE: 27

```
aagcctgaaa agactaggat gtgtgtgtgc gttgtgtgta tgtgtatatg tataggtgtg       60
catgtgtgtt tgcttatata catgtttatt tgtgtaatag tataataagc agtaggaatg     120
gagaaataaa actactgttg tttggatatt tactctcttc taggcagtgt tctggatact    180
ttttagttat tcttccattc tctgcctact ttacattcag tgcatttaag gggttaatga   240
tccatccaac tacagcaata ttttgtcact aaaattcattc tgatttggta tacttggtgg   300
ttttaaaatc aatacatact tcatcttttg gcagtgcctt tactttttga agttagtata   360
aatgagtata aatgctgttt aagtataaac aaatctttta gtcccggagg aagactgaaa    420
ttagcatata tagtaaacat ctttacttag aaaaagaagt tatttttgtt tgtggttttc     480
tagatttaag aaatgtgtct wtgtgtatag ttacacaaat acgttatctc aaatcatatt    540
```

```
tacagtgtat taaaatggat actttacata atttcaaata tagtatgtac aggggctagc    600
attaaagcta caaatagttg agtccaggtc taccaaaagt ggatgcaaga cactttctcc    660
tttttccaga aggaaaatt gtctgttatg tcctgcctct tctatccttg cctagagtaa    720
atttctatta gtatttgcaa tcaatcagct taatgctcta tttatcttat tgagagatga    780
cttctcttta attttatag gttaattaat ttagataact agatcatatg gaagcatcta    840
aatgcatgca aaccagaaga atttctctga ctgtctcggg ttacctgatc atggctgtca    900
cactttggat tctgaaggaa gcagactcta agaatgagtt tggcatgcac taagttgatt    960
ggggaatatt cttggaaagg aaggaagcag gagtagacag a                       1001
```

<210> SEQ ID NO 28
<211> LENGTH: 1001
<212> TYPE: DNA
<213> ORGANISM: Homo sapiens

<400> SEQUENCE: 28

```
gatatttact ctcttctagg cagtgttctg gatactttt agttattctt ccattctctg    60
cctactttac attcagtgca tttaaggggt taatgatcca tccaactaca gcaatatttt   120
gtcactaaat tcattctgat ttggtatact tggtggtttt aaaatcaata catacttcat   180
cttttggcag tgcctttact ttttgaagtt agtataaatg agtataaatg ctgtttaagt   240
ataaacaaat cttttagtcc cggaggaaga ctgaaattag catatatagt aaacatcttt   300
acttagaaaa agaagttatt tttgtttgtg gttttctaga tttaagaaat gtgtctttgt   360
gtatagttac acaaatacgt tatctcaaat catatttaca gtgtattaaa atggatactt   420
tacataattt caaatatagt atgtacaggg gctagcatta aagctacaaa tagttgagtc   480
caggtctacc aaaagtggat rcaagacact ttctcctttt tccagaaagg aaaattgtct   540
gttatgtcct gcctcttcta tccttgccta gagtaaattt ctattagtat ttgcaatcaa   600
tcagcttaat gctctatttta tcttattgag agatgacttc tctttaattt ttataggtta   660 attaattag ataactagat catatggaag catctaaatg catgcaaacc agaagaattt   720
ctctgactgt ctcgggttac ctgatcatgg ctgtcacact ttggattctg aaggaagcag   780
actctaagaa tgagtttggc atgcactaag ttgattgggg aatattcttg gaaggaagg   840 aagcaggagt agacagaggg agaattgggc tgctacatag cctcgatgga gacctctgct   900
gatgccgcag agaattctgg agctagaata cccttcagt gttgtactga gttaggataa    960
ggggaatgag tctttagagc cctgggtcag tcattctatc c                       1001
```

<210> SEQ ID NO 29
<211> LENGTH: 1001
<212> TYPE: DNA
<213> ORGANISM: Homo sapiens

<400> SEQUENCE: 29

```
aaaggaagga agcaggagta gacagaggga gaattgggct gctacatagc ctcgatggag    60
acctctgctg atgccgcaga gaattctgga gctagaataa cccttcagtg ttgtactgag   120
ttaggataag gggaatgagt ctttagagcc ctgggtcagt cattctatcc aaaccactcc   180
aataaaagag cattcagctt tcttcagcta agcagccctc acgtgggttg tcagctaggg   240 cttttctgctg acagcactat cagcagctgg gagaataagt ccatcattcc tgaaaggcaa   300
gcccatggta tcttacaata tccaccaaaa agaccagtaa tatatccatt tctgagaaat   360
```

```
taattattga gctaataaca caggagaagg caaaatggta agaatttatt catcctagag      420
acaaatgagt aggtatcaca aacataatga tcaggaaaag aagccagtca caaaagagta      480
tacatgttat aattccattt ycctaagatt aaagcaaaca aagcacacag atgcacgcct      540
gcgtatgtgc gcgtgcgtgc gcgcgcgcgc acacacacac acacacacac acacacagag      600
agctaaaatt aatgtgtggg ttttagaaga ctcaggataa tgtttacatt tagttttctt      660
tttttaattt ggtagaattt ttgtcattaa tttgttcatt tgttgttat  ttataagtat      720 aaagaatttt taaacacaaa taatctatac ttaattttgt gtgtgtattt atttatttaa      780
gaagcataat aggccaggcg tagtggctca cgcctgtaat cccaacccct tgggaagccg      840
aggcgggtgg atctcctgaa atcaggagtt gaagaccacc ctgggcaaca tggtgaaacc      900
ccgtctctac taaaatacaa aaaattagct gggcatggtg gcgtgagtct gtagtcccag      960
ctactcagga ggctgggcac gagaatcgct tgagccctgg a                          1001
```

<210> SEQ ID NO 30
<211> LENGTH: 1001
<212> TYPE: DNA
<213> ORGANISM: Homo sapiens
<220> FEATURE:
<221> NAME/KEY: modified_base
<222> LOCATION: (501)..(501)
<223> OTHER INFORMATION: a, c, t, g, unknown or other

<400> SEQUENCE: 30

```
ataacccttc agtgttgtac tgagttagga taaggggaat gagtctttag agccctgggt       60
cagtcattct atccaaacca ctccaataaa agagcattca gctttcttca gctaagcagc      120
cctcacgtgg gttgtcagct agggctttct gctgacagca ctatcagcag ctgggagaat      180
aagtccatca ttcctgaaag gcaagcccat ggtatcttac aatatccacc aaaaagacca      240
gtaatatatc catttctgag aaattaatta ttgagctaat aacacaggag aaggcaaaat      300
ggtaagaatt tattcatcct agagacaaat gagtaggtat cacaaacata atgatcagga      360
aaagaagcca gtcacaaaag agtatacatg ttataattcc atttccctaa gattaaagca      420
aacaaagcac acagatgcac gcctgcgtat gtgcgcgtgc gtgcgcgcgc gcacacacac      480
acacacacac acacacacac nagagctaaa attaatgtgt gggttttaga agactcagga      540
taatgtttac atttagtttt cttttttttaa tttggtagaa ttttttgtcat taatttgttc      600 attttgttgt tattttataag tataaagaat ttttaaacac aaataatcta tacttaattt      660
tgtgtgtgta tttatttatt taagaagcat aataggccag gcgtagtggc tcacgcctgt      720
aatcccaacc ctttgggaag ccgaggcggg tggatctcct gaaatcagga gttgaagacc      780
accctgggca acatggtgaa accccgtctc tactaaaata caaaaaatta gctgggcatg      840
gtggcgtgag tctgtagtcc cagctactca ggaggctggg cacgagaatc gcttgagccc      900
tggaggcgga ggttgcagtg agccgcgatt gcaccactgc actccagctt gggccacaga      960
gtaagactct gactaaaaaa aaaaaaaaaa aaaagaagc a                            1001
```

<210> SEQ ID NO 31
<211> LENGTH: 1001
<212> TYPE: DNA
<213> ORGANISM: Homo sapiens
<220> FEATURE:
<221> NAME/KEY: modified_base
<222> LOCATION: (501)..(501)
<223> OTHER INFORMATION: a, c, t, g, unknown or other

<400> SEQUENCE: 31

```
ccataagaaa tagacaacct caaatgagag aagatctgat tgagtagtca ttcaattcta      60
aggccattct gctcaggcat tacacatact ttggcttcct ttttctcat  tttaatcagc     120 aggagaattt acttggaagc aaaatctttg gtttcttaac tattattacc cacctgaagt     180
catcatttct gttattaca  tcataatcat ctctacttgc caccaattgt acattcccaa     240
agagcaaatt atgatttcaa gtgaagacaa tggaacagga acagatgtgc tactgaaaga     300
gagacatcct attatcctgg aaatgtactc cataatgaag aacaaggggga aaagatcag     360 aaggtattgt catatatcaa ataaagtct  gttctagcag caggattaca tttagagaga     420
tctgctgatg tttccatgca ccattcatag tgctttatgc ttgacatttg catactagag     480
aaatagcaaa attagaccaa naaaaaaatc catatgcaca attttttggca aatctcttag    540 tatagccttt gctgcaattt cctttatcct catttggtct tgtcacacca tattgaccct     600
gcttccaatt gcggcacttc tgtgtggttc tgactttctt tttcccaaga cctccgttga     660
attgcaccac cagctatttt aatgatcttc ataaaatatc tgtgtctttt aaccctaagg     720
aagtgaagct gacagaatga agactgtgta actattcaaa ttgttttaa  aaactgatgt     780 ttgtggttac tcggactgtg aagcatgtgt tttatatcaa ttcactcata aatgcagtat     840
tcacttaggc caggcacggt ggcttacgcc tgtaatccca gcactttgaa aggccgagga     900
gggtggatca caaggtcagg agttcgagac cagcctggcc aacatggtga accccgtct     960 ctgctaaaga tacaaaaagt tagccggccg tggtggcagg c                       1001
```

<210> SEQ ID NO 32
<211> LENGTH: 1001
<212> TYPE: DNA
<213> ORGANISM: Homo sapiens
<220> FEATURE:
<221> NAME/KEY: modified_base
<222> LOCATION: (501)..(501)
<223> OTHER INFORMATION: a, c, t, g, unknown or other

<400> SEQUENCE: 32

```
cataagaaat agacaacctc aaatgagaga agatctgatt gagtagtcat tcaattctaa     60
ggccattctg ctcaggcatt acacatactt tggcttcctt ttttctcatt ttaatcagca    120
ggagaattta cttggaagca aaatctttgg tttcttaact attattaccc acctgaagtc    180
atcatttctg tttattacat cataatcatc tctacttgcc accaattgta cattcccaaa    240
gagcaaatta tgatttcaag tgaagacaat ggaacaggaa cagatgtgct actgaaagag    300
agacatccta ttatcctgga aatgtactcc ataatgaaga acaaggggaa aaagatcaga    360
aggtattgtc atatatcaaa ataaagtctg ttctagcagc aggattacat ttagagagat    420
ctgctgatgt ttccatgcac cattcatagt gctttatgct tgacatttgc atactagaga    480
aatagcaaaa ttagaccaaa naaaaaaatc catatgcaca attttttggca aatctcttag   540 tatagccttt gctgcaattt cctttatcct catttggtct tgtcacacca tattgaccct    600
gcttccaatt gcggcacttc tgtgtggttc tgactttctt tttcccaaga cctccgttga    660
attgcaccac cagctatttt aatgatcttc ataaaatatc tgtgtctttt aaccctaagg    720
aagtgaagct gacagaatga agactgtgta actattcaaa ttgttttaa aaactgatgt     780 ttgtggttac tcggactgtg aagcatgtgt tttatatcaa ttcactcata aatgcagtat    840
tcacttaggc caggcacggt ggcttacgcc tgtaatccca gcactttgaa aggccgagga    900
gggtggatca caaggtcagg agttcgagac cagcctggcc aacatggtga accccgtct    960
```

```
ctgctaaaga tacaaaaagt tagccggccg tggtggcagg c                      1001
```

<210> SEQ ID NO 33
<211> LENGTH: 1001
<212> TYPE: DNA
<213> ORGANISM: Homo sapiens

<400> SEQUENCE: 33

```
atcagcagga gaatttactt ggaagcaaaa tctttggttt cttaactatt attacccacc    60
tgaagtcatc atttctgttt attacatcat aatcatctct acttgccacc aattgtacat   120
tcccaaagag caaattatga tttcaagtga agacaatgga acaggaacag atgtgctact   180
gaaagagaga catcctatta tcctggaaat gtactccata atgaagaaca aggggaaaaa   240
gatcagaagg tattgtcata tatcaaaata aagtctgttc tagcagcagg attacattta   300
gagagatctg ctgatgtttc catgcaccat tcatagtgct ttatgcttga catttgcata   360
ctagagaaat agcaaaatta gaccaaaaga aaaaaatcca tatgcacaat tttttggcaaa  420
tctcttagta tagcctttgc tgcaatttcc tttatcctca tttggtcttg tcacaccata   480
ttgaccctgc ttccaattgc rgcacttctg tgtggttctg actttctttt tcccaagacc   540
tccgttgaat tgcaccacca gctattttaa tgatcttcat aaaatatctg tgtcttttaa   600
ccctaaggaa gtgaagctga cagaatgaag actgtgtaac tattcaaatt gttttttaaaa  660
actgatgttt gtggttactc ggactgtgaa gcatgtgttt tatatcaatt cactcataaa   720
tgcagtattc acttaggcca ggcacggtgg cttacgcctg taatcccagc actttgaaag   780
gccgaggagg gtggatcaca aggtcaggag ttcgagacca gcctggccaa catggtgaaa   840
ccccgtctct gctaaagata caaaaagtta gccggccgtg gtggcaggcg cctgtaatcc   900
caggtactcg ggaggctgag gcagaatcgc ttgaacctgg gaggtagagg tttcagtgag   960
gcgagattgt gccattgcac tccagcctgg gcgacagggc g                     1001
```

<210> SEQ ID NO 34
<211> LENGTH: 1001
<212> TYPE: DNA
<213> ORGANISM: Homo sapiens

<400> SEQUENCE: 34

```
gagagacatc ctcagaggaa ttacagttca ctcgccacaa ggcacaggcc tgtggtacaa    60
gtctgagcta gaacattaag tcaataagcc tatactcatt tttctcatgt tgctttctca   120
ctcgcctatc ctaccttgct ctaaacttcc catctgtctg tagaactgtg gcttaaaaaa   180
aagataaaaa actgcagaga ggagagagga gaaaggcaga gcagacctaa aaatcacaaa   240
ctgtgtgatg taaagtgtca actggcagat acacactacc gccaggtgga aacacggaac   300
ctagggagag ggagctgaag tccactgctc ttatctagag aagtctcaga taatcctgcc   360
aactgggaag ggaacaaggg cctagcgcag tttaaaggtg gagatggcac gtcccagtgc   420
gcagagagca gaagtagaga gaacttctca ggagagatcc ccttaaatta gcattaaatt   480
actcatttag ggcctggcgc rgttgctcac gcctgtaatc ccagcacttt aggaggccga   540
ggagggcaga tccgaggtc aagagatcaa gaccatcctg cccaacatgg tgaaacccaa    600
cctctactaa aaatacaaaa attagctggg cgtggtggcg cacgcctgtt gtcccagcta   660
ttcaggaggc tgaggcagga aaatcgctag aacctgggag gtggaggttg cagtgagccg   720
agatagcacc actgcactac agcctggtga caaggcaaga ctccatctca agaaaagaaa   780
aaaatactaa tttagttgca agagtggagg cgaggaagat gagaattatg aaaaggggca   840
```

```
cctacatact taaaacacaa tttcactgac atttatttac tgtttatact tggatagaat      900
ataaagaaaa caagattcta ccccgctcta gcaaggagaa agctaacatt atgcatgcac      960
taagctcaca tgcatatact atttcattta atcctcacaa c                         1001

<210> SEQ ID NO 35
<211> LENGTH: 1001
<212> TYPE: DNA
<213> ORGANISM: Homo sapiens

<400> SEQUENCE: 35
atatccagag ggagagagaa tgatattact cccaatatcg tagaagtgta cagccccct       60 gtgatattgt tcttaatatc cgtggggtga gtatgatatt actcccaata tagaaggggg     120
aagtacaccc tcctgtgata ctgttcctaa tatccaccgg gggtgagaat gatattactc     180
ccaatatcgc aggaggtgta catccctctg tcacattgtt cgtaatgttt aacgggaaag     240
ataatattac tcgaaatatc gttaataccc tgtgtgtcca ccccctgtg atataattag      300 taatatccag ggggagagga aggtgatatt actccccatg tcacgggggg tgtccaccct     360
cctgtgatat gatccgtaat atccaggtg gagaggggg gcgatattac tctcaatgtc      420
gcggggggtg tccacccccc tgtgatatgg tttgtaatat ccggggggcgg agagggcat    480 gatattactc tcaatatctt rcgcaccgtt tttgtacacc ctctctgata tagtttgcaa    540
tatccaggaa gggagaggat gatattactc cccatatcgc aggggggtgtg cacctctctg    600 tgacagcgtt tgtattatcg gtggggaagt gtatgatata attccctata tcgcagaagg    660
tgtacacgcc cttgtgatat tgttcataat atccagttgg agagggatg atattactcc     720 ccatttgcag ggggcggaca cccttctgtg atattgttcg tactatccgg gaggtgggga    780
gaggatgata ttactcttca tattgcaggg agtgtacacc ccctatgat attttttattc    840 tacccaaggg gggtagaggt tgatattact ccccatgact cagggggtgta caccccctg    900 tgatatttt tgtaatgtcc aaggtggggc agaggatatt acttcccatg tctgataggg    960
tgtacacgcc tttgtgatat tgtttgtaat atccagagtg g                        1001
```